United States Patent
Guo et al.

(10) Patent No.: US 11,034,661 B2
(45) Date of Patent: Jun. 15, 2021

(54) SUBSTITUTED N'-HYDROXYCARBAMIMIDOYL-1,2,5-OXADIAZOLE COMPOUNDS AS INDOLEAMINE 2,3-DIOXYGENASE IDO INHIBITORS

(71) Applicants: Merck Sharp & Dohme Corp., Rahway, NJ (US); Liangqin Guo, Monroe Township, NJ (US); Yongxin Han, Needham, MA (US); Kun Liu, Needham, MA (US); Shuwen He, Fanwood, NJ (US); Joseph Kozlowski, Princeton, NJ (US); Ravi Nargund, East Brunswick, NJ (US); Wensheng Yu, Edison, NJ (US); Hongjun Zhang, Boston, MA (US); Qinglin Pu, Needham, MA (US); Derun Li, Brighton, MA (US); Abdelghani Achab, Melrose, MA (US); Guoqing Li, Belle Mead, NJ (US)

(72) Inventors: Liangqin Guo, Monroe Township, NJ (US); Yongxin Han, Needham, MA (US); Kun Liu, Needham, MA (US); Shuwen He, Fanwood, NJ (US); Joseph Kozlowski, Princeton, NJ (US); Ravi Nargund, East Brunswick, NJ (US); Wensheng Yu, Edison, NJ (US); Hongjun Zhang, Boston, MA (US); Qinglin Pu, Needham, MA (US); Derun Li, Brighton, MA (US); Abdelghani Achab, Melrose, MA (US); Guoqing Li, Belle Mead, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 16/495,883

(22) PCT Filed: Mar. 23, 2018

(86) PCT No.: PCT/US2018/023912
§ 371 (c)(1),
(2) Date: Sep. 20, 2019

(87) PCT Pub. No.: WO2018/183097
PCT Pub. Date: Oct. 4, 2018

(65) Prior Publication Data
US 2020/0102278 A1    Apr. 2, 2020

Related U.S. Application Data

(60) Provisional application No. 62/478,262, filed on Mar. 29, 2017.

(51) Int. Cl.
*C07D 271/08* (2006.01)
*C07D 413/12* (2006.01)

(52) U.S. Cl.
CPC ......... *C07D 271/08* (2013.01); *C07D 413/12* (2013.01)

(58) Field of Classification Search
CPC ............................ C07D 271/08; C07D 413/12
See application file for complete search history.

(56) References Cited

U.S. PATENT DOCUMENTS

| | | | |
|---|---|---|---|
| 2007/0173524 | A1 | 7/2007 | Prendergast et al. |
| 2010/0015178 | A1 | 1/2010 | Combs et al. |
| 2011/0165188 | A1 | 7/2011 | Combs et al. |

FOREIGN PATENT DOCUMENTS

| | | |
|---|---|---|
| WO | 2007075598 A2 | 7/2007 |
| WO | WO2018044663 A1 | 3/2018 |
| WO | 2018156443 A1 | 8/2018 |

OTHER PUBLICATIONS

European Search Report, PCTUS2018023912, dated Sep. 1, 2020, 5 pages.
Austin, Christopher, J. D. et al., Carborane-Containing Hydroxyamidine Scaffolds as Novel Inhibitors of Indoleamine 2,3-Dioxygenase 1 (IDO1), Aust. J. Chem., 2015, p. 1866-1870, vol. 68.

*Primary Examiner* — Kamal A Saeed
(74) *Attorney, Agent, or Firm* — Yong Zhao; Anna L. Cocuzzo

(57) ABSTRACT

Disclosed herein is a compound of formula (I), or a pharmaceutically acceptable salt thereof. Also disclosed herein are uses of the compounds disclosed herein in the potential treatment or prevention of an IDO-associated disease or disorder. Also disclosed herein are compositions comprising a compound disclosed herein. Further disclosed herein are uses of the compositions in the potential treatment or prevention of an IDO-associated disease or disorder.

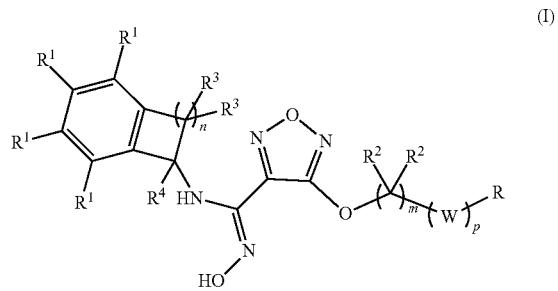

(I)

19 Claims, No Drawings

SUBSTITUTED N'-HYDROXYCARBAMIMIDOYL-1,2,5-OXADIAZOLE COMPOUNDS AS INDOLEAMINE 2,3-DIOXYGENASE IDO INHIBITORS

CROSS REFERENCE TO RELATED APPLICATIONS

The present application is the 371 national phase application of International Application No. PCT/US2018/023912, filed Mar. 23, 2018, which claims the benefit of U.S. Provisional Application No. 62/478,262, filed Mar. 29, 2017, hereby incorporated by reference in their entirety.

BACKGROUND OF THE INVENTION

Tryptophan (Trp) is an essential amino acid required for the biosynthesis of proteins, niacin and the neurotransmitter 5-hydroxytryptamine (serotonin). The enzyme indoleamine 2,3-dioxygenase (IDO) catalyzes the first and rate limiting step in the degradation of L-tryptophan to N-formyl-kynurenine. In human cells, a depletion of Trp resulting from IDO activity is a prominent gamma interferon (EFN-γ)-inducible antimicrobial effector mechanism. IFN-γ stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process (Daubener, et al, 1999, Adv. Exp. Med. Biol, 467: 517-24; Taylor, et al, 1991, FASEB J., 5: 2516-22).

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL2) was believed to result from IDO released by the tumor cells in response to IFN-γ secretion by the PBLs. This effect was reversed by treatment with 1-methyl-tryptophan (IMT), a specific IDO inhibitor. It was proposed that IDO activity in tumor cells may serve to impair antitumor responses (Logan, et al, 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. For example, increased levels of IFNs and elevated levels of urinary Trp metabolites have been observed in autoimmune diseases; it has been postulated that systemic or local depletion of Trp occurring in autoimmune diseases may relate to the degeneration and wasting symptoms of these diseases. In support of this hypothesis, high levels of IDO were observed in cells isolated from the synovia of arthritic joints. IFNs are also elevated in human immunodeficiency virus (HIV) patients and increasing IFN levels are associated with a worsening prognosis. Thus, it was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol, 294: 425-35). To this end, it has recently been shown that IDO inhibition can enhance the levels of virus-specific T cells and, concomitantly, reduce the number of virally-infected macrophages in a mouse model of HIV (Portula et al., 2005, Blood, 106: 2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to IMT, and a rapid, T cell-induced rejection of all allogeneic conception was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Moan, et al., 1998, Science, 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al, 2005, Nature Med., 11: 312-9).

One mechanism contributing to immunologic unresponsiveness toward tumors may be presentation of tumor antigens by tolerogenic host APCs. A subset of human IDO-expressing antigen-presenting cells (APCs) that coexpressed CD 123 (IL3RA) and CCR6 and inhibited T-cell proliferation have also been described. Both mature and immature CD 123-positive dendritic cells suppressed T-cell activity, and this IDO suppressive activity was blocked by IMT (Munn, et al, 2002, Science, 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest, 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al, 2003, Trends Immunol, 24: 242-8). In states of persistent immune activation, availability of free serum Trp is diminished and, as a consequence of reduced serotonin production, serotonergic functions may also be affected (Wirleitner, et al., 2003, Curr. Med. Chem., 10: 1581-91).

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. Compounds disclosed herein are useful in the potential treatment or prevention of IDO-related diseases.

SUMMARY OF THE INVENTION

Disclosed herein are novel compounds of formula (I) which are inhibitors of the IDO enzyme. Also disclosed herein are uses of these compounds in the potential treatment or prevention of an IDO-associated disease or disorder. Also disclosed herein are compositions comprising one or more of the compounds. Further disclosed herein are uses of these compositions in the potential prevention or treatment of an IDO-associated disease or disorder.

DETAILED DESCRIPTION OF THE INVENTION

Disclosed herein is a compound of formula (I), or a pharmaceutically acceptable salts thereof:

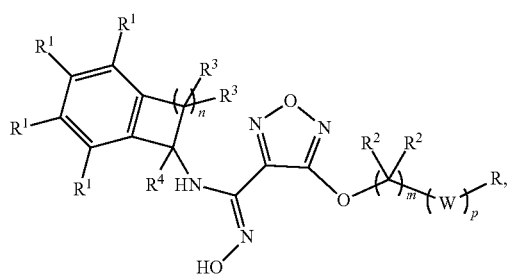

(I)

wherein: m is 0, 1, 2, 3 or 4; n is 1, 2, or 3; p is 0, 1, 2 or 3;

W is selected from (a) —$CR^aR^b$— and (b) —$NR^a$—; wherein each $R^a$ and $R^b$ is independently selected from the group consisting of (a) hydrogen, (b) halogen and (c) $C_{1-6}$ alkyl, optionally substituted with —OH or halogen;

R is selected from the group consisting of:
(a) hydrogen;
(b) $C_{1-6}$alkyl, optionally substituted with one to three substituents independently selected from the group consisting of (i) —OH, (ii) halogen, and (iii) —$NH_2$;
(c) $C_{3-6}$cycloalkyl, optionally substituted with one to three substituents independently selected from the group consisting of (i) —OH and (ii) —$C_{1-6}$alkyl, optionally substituted with —OH;
(d) —(C=O)—(NH)$_q$—$R^c$, wherein q is 0 or 1; and $R^c$ is selected from the group consisting of:
(i) hydrogen,
(ii) —$C_{1-6}$alkyl, optionally substituted with one to three substituents independently selected from the group consisting of (1) halogen, (2) —OH, (3) —O-methyl, (4) —$C_{3-6}$cycloalkyl, (5) —CN, (6) —$S(O)_2$—$C_{1-6}$alkyl and (7) heterocyclyl,
(iii) —O—$C_{1-6}$alkyl,
(iv) —OH,
(v) —$C_{3-6}$cycloalkyl, optionally substituted with —OH or —$C_{1-6}$alkyl, and
(vi) a 4-, 5- or 6-membered heterocyclyl, optionally substituted with one to four substituents independently selected from the group consisting of (1) halogen, (2) $C_{1-6}$alkyl and (3) —OH;
(e) —$S(O)_2$—$NR^dR^e$; each of $R^d$ and $R^e$ is independently hydrogen or $C_{1-6}$alkyl;
(f) —$S(O)_2$—$C_{1-6}$alkyl;
(g) $C_{4-5}$cycloalkenyl, optionally substituted with one to four substituents independently selected from the group consisting of (i) oxo, (ii) —$C_{1-6}$alkyl and (iii) —NH—$C_{1-6}$alkyl; and
(h) a 4-, 5- or 6-membered heterocyclyl, optionally substituted with one to four substituents independently selected from the group consisting of (i) halogen, (ii) $C_{1-6}$ alkyl, (iii) oxo and (iv) —C(O)—$C_{1-6}$alkyl, optionally substituted with —OH;

each occurrence of $R^1$ is independently selected from the group consisting of (a) hydrogen, (b) halogen, (c) —CN, (d) $C_{1-6}$ alkyl, optionally substituted with 1 to 3 halogens, and (e) —O—$C_{1-6}$alkyl, optionally substituted with one to three halogens;

each occurrence of $R^2$ is independently selected from the group consisting of (a) hydrogen, (b) halogen, (c) —OH and (d) $C_{1-6}$alkyl, optionally substituted with —OH;

or, alternatively, two $R^2$ groups together with the carbon to which they are attached form a $C_{3-6}$ cycloalkyl or 4-, 5-, or 6-membered heterocycle;

or, alternatively, $R^2$ and $R^a$ of W together with the carbon and/or nitrogen atoms to which they are attached form a 4-, 5- or 6-membered carbocycle or heterocycle;

each occurrence of $R^3$ is independently selected from the group consisting of (a) hydrogen, (b) halogen, (c) $C_{1-6}$ alkyl and (d) —O—$C_{1-6}$ alkyl; and $R^4$ is selected from the group consisting of (a) hydrogen and (b) $C_{1-6}$ alkyl.

In one embodiment of the compound of formula (I), or a pharmaceutically acceptable salt thereof:
m is 1 or 2; n is 1 or 2; and p is 0, 1 or 2;
W is selected from (a) —$CR^aR^b$— and (b) —$NR^a$—; wherein each occurrence of $R^a$ and $R^b$ is independently selected from the group consisting of (a) hydrogen and (b) $C_{1-6}$ alkyl, optionally substituted with —OH;

R is selected from the group consisting of:
(a) hydrogen;
(b) $C_{1-6}$alkyl, optionally substituted with one to three substituents independently selected from the group consisting of (i) —OH and (ii) halogen;
(c) $C_{3-6}$cycloalkyl, optionally substituted with —OH;
(d) —(C=O)—(NH)$_q$—R, wherein q is 0 or 1; and $R^c$ is selected from the group consisting of:
  (i) hydrogen,
  (ii) —$C_{1-6}$alkyl, optionally substituted with one to three substituents independently selected from the group consisting of (1) halogen, (2) —OH, (3) —O-methyl and (4) —$C_{3-6}$cycloalkyl,
  (iii) —O—$C_{1-6}$alkyl, and
  (iv) a 5- or 6-membered heterocyclyl, optionally substituted with one to four substituents independently selected from the group consisting of (1) halogen, (2) $C_{1-6}$alkyl and (3) —OH;
(e) —S(O)$_2$—NH$_2$;
(f) —S(O)$_2$—$C_{1-6}$alkyl; and
(g) a 4-, 5- or 6-membered heterocyclyl, optionally substituted with one to four substituents independently selected from the group consisting of (i) halogen, (ii) $C_{1-6}$ alkyl, (iii) oxo and (iv) —C(O)—$C_{1-6}$alkyl, optionally substituted with —OH;

each occurrence of $R^1$ is independently selected from the group consisting of (a) hydrogen, (b) halogen, and (c) —CN;
each occurrence of $R^2$ is independently selected from the group consisting of (a) hydrogen and (b) —OH;
or alternatively, two $R^2$ groups together with the carbon to which they are attached form a $C_{3-6}$ cycloalkyl or a 4-, 5-, or 6-membered heterocycle;
or alternatively, $R^2$ and $R^a$ of W together with the carbon and/or nitrogen atoms to which they are attached form a 4-, 5- or 6-membered carbocycle or heterocycle;
each occurrence of $R^3$ is independently selected from the group consisting of (a) hydrogen and (b) $C_{1-6}$ alkyl; and
$R^4$ is selected from the group consisting of (a) hydrogen and (b) $C_{1-6}$ alkyl.

In one embodiment of the compound described above, or a pharmaceutically acceptable salt thereof:
R is selected from the group consisting of:
(a) hydrogen;
(b) $C_{1-6}$alkyl, optionally substituted with one to three —OH;
(c) $C_{3-6}$cycloalkyl, optionally substituted with —OH;
(d) —(C=O)—(NH)$_q$—R, wherein q is 0 or 1; and R is selected from the group consisting of:
  (i) hydrogen,
  (ii) —$C_{1-6}$alkyl, optionally substituted with one to three substituents independently selected from the group consisting of (1) halogen, (2) —OH and (3) heterocyclyl,
  (iii) —O—$C_{1-6}$alkyl, and
  (iv) a 5- or 6-membered heterocyclyl, optionally substituted with one to four substituents independently selected from the group consisting of (1) halogen, (2) $C_{1-6}$alkyl and (3) —OH;
(e) —S(O)$_2$—NH$_2$;
(f) —S(O)$_2$—$C_{1-4}$alkyl; and
(g) a 5- or 6-membered heterocyclyl, optionally substituted with one to four substituents independently selected from the group consisting of (i) halogen, (ii) $C_{1-6}$alkyl and (iii) oxo; and each occurrence of $R^a$ and $R^b$ is independently selected from the group consisting of (a) hydrogen and (b) $C_{1-4}$ alkyl, optionally substituted with —OH.

In one embodiment of the compound described above, or a pharmaceutically acceptable salt thereof, R is a 5- or 6-membered heterocyclyl selected from the group consisting of pyridinyl, pyrimidinyl, piperidinyl, pyrrolidinyl, triazolyl and thiazolyl; wherein the 5- or 6-membered heterocyclyl is optionally substituted with one to four substituents independently selected from the group consisting of (i) $C_{1-6}$alkyl and (ii) oxo.

In one embodiment of the compound described above, or a pharmaceutically acceptable salt thereof, each occurrence of $R^1$ is independently selected from the group consisting of (a) hydrogen and (b) halogen.

In one embodiment of the compound described above, or a pharmaceutically acceptable salt thereof, each occurrence of $R^2$ is independently selected from the group consisting of (a) hydrogen and (b) —OH.

In one embodiment of the compound described above, or a pharmaceutically acceptable salt thereof, each occurrence of $R^3$ is independently selected from the group consisting of (a) hydrogen and (b) $C_{1-6}$ alkyl.

In one embodiment of the compound described above, or a pharmaceutically acceptable salt thereof, m is 1 or 2; n is 1; and p is 0, 1 or 2;
W is selected from (a) —$CR^aR^b$— and (b) —$NR^a$—; wherein each occurrence of $R^a$ and $R^b$ is independently selected from the group consisting of (i) hydrogen and (ii) $C_{1-6}$alkyl;
R is selected from the group consisting of:
(a) hydrogen;
(b) $C_{1-6}$alkyl, optionally substituted with one to three —OH;
(c) $C_{3-6}$cycloalkyl, optionally substituted with —OH;
(d) —(C=O)—(NH)$_q$—R, wherein q is 0 or 1; and R is selected from the group consisting of:
  (i) hydrogen,
  (ii) —$C_{1-6}$alkyl, optionally substituted with one to three —OH,
  (iii) —O—$C_{1-6}$alkyl, and
  (iv) a 5- or 6-membered heterocyclyl selected from the group consisting of pyridinyl, pyrimidinyl, piperidinyl, pyrrolidinyl, triazolyl and thiazolyl;
(e) —S(O)$_2$—NH$_2$;
(f) —S(O)$_2$—$C_{1-6}$alkyl; and
(g) a 5- or 6-membered heterocyclyl selected from the group consisting of pyridinyl, pyrimidinyl, piperidinyl, pyrrolidinyl, triazolyl and thiazolyl;
each occurrence of $R^1$ is independently selected from the group consisting of (a) hydrogen and (b) halogen;
each occurrence of $R^2$ is independently selected from the group consisting of (a) hydrogen and (b) —OH;
or alternatively, two $R^2$ groups together with the carbon to which they are attached form a $C_{3-6}$ cycloalkyl or 4-, 5-, or 6-membered heterocycle;
or alternatively, $R^2$ and $R^a$ of W together with the carbon and/or nitrogen atoms to which they are attached form a 4-, 5- or 6-membered carbocycle or heterocycle;
each occurrence of $R^3$ is hydrogen; and
$R^4$ is selected from the group consisting of (a) hydrogen and (b) $C_{1-6}$ alkyl.

In one embodiment, a compound of formula (I) has formula (Ia), or a pharmaceutically acceptable salt thereof:

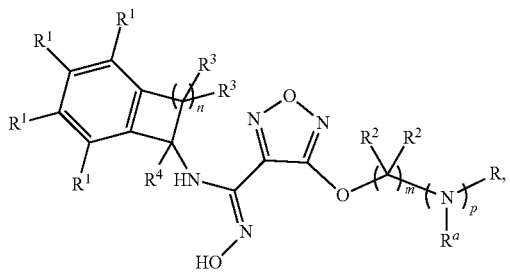

(Ia)

wherein: m is 1, 2, or 3; n is 1 or 2; p is 0 or 1;
R is selected from the group consisting of:
(a) $C_{1-6}$alkyl, optionally substituted with one to three substituents independently selected from the group consisting of (i) —OH and (ii) halogen,
(b) $C_{3-6}$cycloalkyl, optionally substituted with —OH,
(c) —(C=O)—(NH)$_q$—R$^c$, wherein q is 0 or 1; and R$^c$ is selected from the group consisting of:
 (i) hydrogen,
 (ii) —$C_{1-6}$alkyl, optionally substituted with one to three substituents independently selected from the group consisting of (1) halogen, (2) —OH and (3) heterocyclyl,
 (iii) —O—$C_{1-6}$alkyl,
 (iv) —$C_{3-6}$cycloalkyl, optionally substituted with —OH, and
 (v) a 5- or 6-membered heterocyclyl, optionally substituted with one to four substituents independently selected from the group consisting of (1) halogen, (2) $C_{1-6}$alkyl and (3) —OH;
(d) —S(O)$_2$—NR$^d$R$^e$; each of R$^d$ and R$^e$ is independently hydrogen or $C_{1-6}$alkyl;
(e) —S(O)$_2$—$C_{1-6}$alkyl; and
(f) a 5- or 6-membered heterocyclyl, optionally substituted with one to four substituents independently selected from the group consisting of (i) halogen and (ii) $C_{1-6}$alkyl;
R$^a$ is selected from the group consisting of (a) hydrogen and (b) $C_{1-6}$ alkyl, optionally substituted with —OH,
each occurrence of R$^1$ is independently selected from the group consisting of (a) hydrogen, (b) halogen and (c) $C_{1-6}$alkyl;
each occurrence of R$^2$ is independently selected from the group consisting of (a) hydrogen, (b) —OH and (c) $C_{1-6}$alkyl, optionally substituted with —OH; and
each occurrence of R$^3$ is independently selected from the group consisting of (a) hydrogen and (b) $C_{1-6}$alkyl.

In one embodiment of the compound of formula (Ia), or a pharmaceutically acceptable salt thereof:
m is 1 or 2; n is 1; p is 0 or 1;
R is selected from the group consisting of:
(a) $C_{1-6}$alkyl, optionally substituted with one to three substituents independently selected from the group consisting of (i) —OH and (ii) halogen,
(b) —(C=O)—(NH)$_q$—R, wherein q is 0 or 1; and R$^c$ is selected from the group consisting of:
 (i) hydrogen,
 (ii) —$C_{1-6}$alkyl, optionally substituted with one to three substituents independently selected from the group consisting of (1) halogen and (2) —OH, (iii) —$C_{3-6}$cycloalkyl, optionally substituted with —OH, and
(iv) a 5- or 6-membered heterocyclyl, optionally substituted with one to four substituents independently selected from the group consisting of (1) halogen, (2) $C_{1-6}$alkyl and (3) —OH;
(c) —S(O)$_2$—NH$_2$;
(d) —S(O)$_2$—$C_{1-6}$alkyl; and
(e) a 5- or 6-membered heterocyclyl selected from pyridinyl, pyrimidinyl, piperidinyl, pyrrolidinyl, triazolyl, and thiazolyl;
R$^a$ is selected from the group consisting of (a) hydrogen and (b) $C_{1-6}$ alkyl, optionally substituted with —OH;
each occurrence of R$^1$ is independently selected from the group consisting of (a) hydrogen, (b) halogen and (c) $C_{1-6}$alkyl;
each occurrence of R$^2$ is independently selected from the group consisting of (a) hydrogen, (b) —OH and (c) $C_{1-4}$alkyl, optionally substituted with —OH; and
each occurrence of R$^3$ is independently selected from the group consisting of (a) hydrogen and (b) $C_{1-6}$alkyl.

In one embodiment, a compound of formula (I) has formula (Ib), or a pharmaceutically acceptable salt thereof:

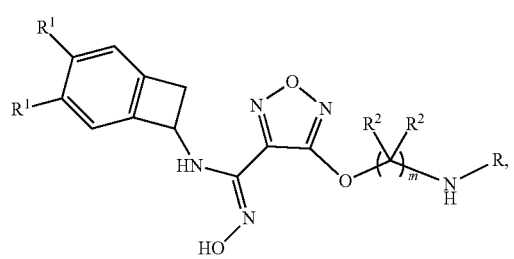

(Ib)

wherein: m is 1 or 2;
R is selected from the group consisting of:
(a) —(C=O)—(NH)$_q$—R, wherein q is 0 or 1; and R$^c$ is selected from the group consisting of:
 (i) hydrogen,
 (ii) —$C_{1-6}$alkyl, optionally substituted with one to two —OH,
 (iii) —$C_{3-6}$cycloalkyl, optionally substituted with —OH; and
(b) —S(O)$_2$—NH$_2$; and
(c) —S(O)$_2$—$C_{1-6}$alkyl;
each occurrence of R$^1$ is independently selected from the group consisting of (a) hydrogen and (b) halogen; and
each occurrence of R$^2$ is independently selected from the group consisting of (a) hydrogen and (b) —OH.

In one embodiment of the compound of formula (Ib), or a pharmaceutically acceptable salt thereof:
m is 2;
R is selected from the group consisting of: (a) —S(O)$_2$—NH$_2$, (b) —S(O)$_2$—CH$_3$, (c) —S(O)$_2$—CH$_2$CH$_3$ and (d) —S(O)$_2$—CH$_2$CH$_2$CH$_3$
R$^1$ is selected from the group consisting of (a) hydrogen, (b) —F and (c) —Cl; and
each occurrence of R$^2$ is hydrogen.

In one embodiment, a compound of formula (I) has formula (Ic), or a pharmaceutically acceptable salt thereof:

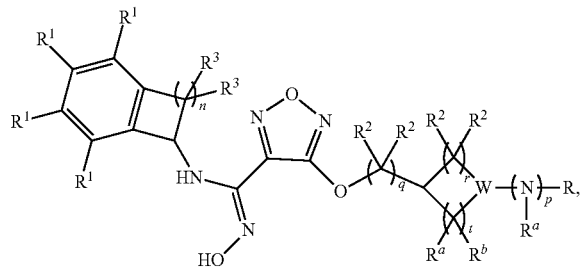

(Ic)

wherein: n is 1 or 2; p is 0 or 1; q is 0, 1 or 2; r is 1 or 2; t is 0, 1 or 2;
W is N or CR$^a$; provided when W is N, p is 0;
R is selected from the group consisting of:
 (a) hydrogen,
 (b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and
  (iv) a 5- or 6-membered heterocyclyl, optionally substituted with one to four substituents independently selected from the group consisting of (1) halogen, (2) C$_{1-6}$alkyl and (3) —OH;
 (c) —S(O)$_2$—NR$^d$R$^e$; each of R$^d$ and R$^e$ is independently hydrogen or C$_{1-6}$alkyl; and
 (d) —S(O)$_2$—C$_{1-6}$alkyl;
each occurrence of R$^a$ and R$^b$ is independently selected from the group consisting of (a) hydrogen and (b) C$_{1-6}$ alkyl, optionally substituted with —OH;
each occurrence of R$^1$ is independently selected from the group consisting of (a) hydrogen and (b) halogen;
each occurrence of R$^2$ is independently selected from the group consisting of (a) hydrogen and (b) —OH; and
each occurrence of R$^3$ is independently selected from the group consisting of (a) hydrogen and (b) C$_{1-6}$alkyl.

In one embodiment of the compound of formula (Ic), or a pharmaceutically acceptable salt thereof:
n is 1 or 2; p is 0 or 1; q is 0; r is 1 or 2; t is 0, 1 or 2;
W is N or CR$^a$; provided when W is N, p is 0;
R is selected from the group consisting of:
 (a) hydrogen,
 (b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and
  (iv) a 5- or 6-membered heterocyclyl selected from pyridinyl, pyrimidinyl, piperidinyl, pyrrolidinyl, triazolyl and thiazolyl;
 (c) —S(O)$_2$—NH$_2$; and
 (d) —S(O)$_2$—C$_{1-4}$alkyl;
each occurrence of R$^a$ and R$^b$ is hydrogen;
each occurrence of R$^1$ is independently selected from the group consisting of (a) hydrogen and (b) halogen;
each occurrence of R$^2$ is independently selected from the group consisting of (a) hydrogen and (b) —OH; and
each occurrence of R$^3$ is hydrogen.

In one embodiment, a compound of formula (I) has formula (Id), or a pharmaceutically acceptable salt thereof:

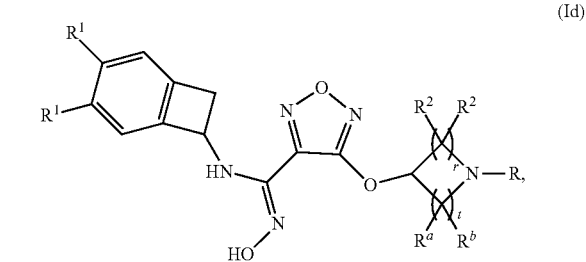

(Id)

wherein: r is 1 or 2; t is 1 or 2;
R is selected from the group consisting of:
 (a) hydrogen;
 (b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and
  (iv) a 5- or 6-membered heterocyclyl selected from pyridinyl, pyrimidinyl, piperidinyl, triazolyl and thiazolyl;
 (c) —S(O)$_2$—NH$_2$; and
 (d) —S(O)$_2$—C$_{1-4}$alkyl;
each occurrence of R$^a$ and R$^b$ is independently selected from the group consisting of (a) hydrogen and (b) C$_{1-4}$alkyl;
each occurrence of R$^1$ is independently selected from the group consisting of (a) hydrogen and (b) halogen; and
each occurrence of R$^2$ is independently selected from the group consisting of (a) hydrogen and (b) —OH.

In one embodiment, a compound of formula (I) has formula (Ie), or a pharmaceutically acceptable salt thereof:

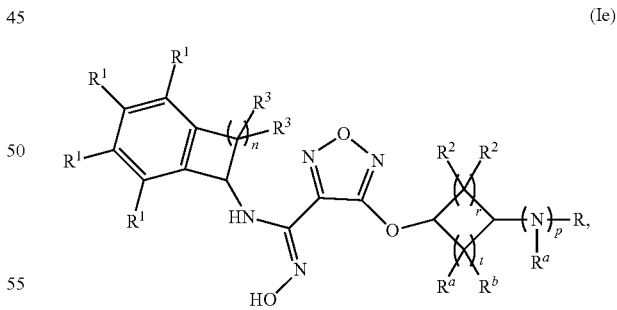

(Ie)

wherein: n is 1 or 2; p is 0 or 1; r is 1 or 2; t is 0, 1 or 2;
R is selected from the group consisting of:
 (a) hydrogen,
 (b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and (iv) a 5- or 6-membered heterocyclyl, optionally substituted with one to four substituents independently selected from the group consisting of (1) halogen, (2) $C_{1-6}$alkyl and (3) —OH;
(c) —S(O)$_2$—NR$^d$R$^e$; each of R$^d$ and R$^e$ is independently hydrogen or $C_{1-6}$alkyl; and
(d) —S(O)$_2$—$C_{1-6}$alkyl;
each occurrence of R$^a$ and R$^b$ is independently selected from the group consisting of (a) hydrogen and (b) $C_{1-6}$ alkyl, optionally substituted with —OH;
each occurrence of R$^1$ is independently selected from the group consisting of (a) hydrogen and (b) halogen;
each occurrence of R$^2$ is independently selected from the group consisting of (a) hydrogen and (b) —OH; and
each occurrence of R$^3$ is independently selected from the group consisting of (a) hydrogen and (b) $C_{1-6}$alkyl.

In one embodiment, a compound of formula (I) has formula (If), or a pharmaceutically acceptable salt thereof:

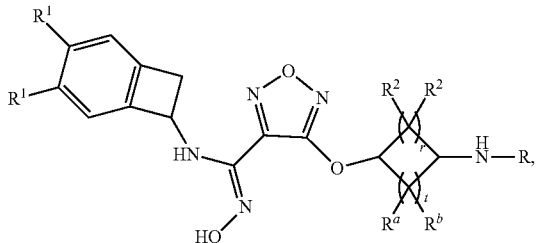

(If)

wherein: r is 1 or 2; t is 0, 1 or 2;
R is selected from the group consisting of:
  (a) hydrogen,
  (b) —(C=O)—R$^c$, wherein R$^c$ is selected from the group consisting of:
    (i) hydrogen,
    (ii) —$C_{1-6}$alkyl, optionally substituted with one to three substituents independently selected from the group consisting of (1) halogen and (2) —OH,
    (iii) —O—$C_{1-6}$alkyl, and
    (iv) a 5- or 6-membered heterocyclyl selected from pyridinyl, pyrimidinyl, piperidinyl, pyrrolidinyl, triazolyl and thiazolyl;
  (c) —S(O)$_2$—NH$_2$; and
  (d) —S(O)$_2$—$C_{1-6}$alkyl;
each occurrence of R$^a$ and R$^b$ is hydrogen;
each occurrence of R$^1$ is independently selected from the group consisting of (a) hydrogen and (b) halogen; and
each occurrence of R$^2$ is hydrogen.

In one embodiment, a compound disclosed herein is selected from the group consisting of the compounds exemplified in Examples 1 to 67; or a pharmaceutically acceptable salt thereof.

Also disclosed herein is a pharmaceutical composition comprising a compound of formula I, (Ia), or (Ib) and at least one pharmaceutically acceptable carrier.

Also disclosed herein is a method of inhibiting activity of indoleamine 2,3-dioxygenase (IDO) comprising contacting IDO with a compound of formula I, (Ia), or (Ib), or a pharmaceutically acceptable salt thereof.

Also disclosed herein is a method of inhibiting immunosuppression in a patient comprising administering to said patient an effective amount of a compound of formula I, (Ia), or (Ib), or a pharmaceutically acceptable salt thereof.

Also disclosed herein is a method of treating cancer, viral infection, depression, a neurodegenerative disorder, trauma, age-related cataracts, organ transplant rejection, or an autoimmune disease in a patient comprising administering to said patient an effective amount of a compound of formula I, (Ia), or (Ib), or a pharmaceutically acceptable salt thereof.

Also disclosed herein is a method of treating melanoma in a patient comprising administering to said patient an effective amount of a compound of Formula I, or a pharmaceutically acceptable salt thereof.

Further disclosed herein is a compound of formula I, (Ia), or (Ib), or a pharmaceutically acceptable salt thereof, for use in therapy. In one embodiment, disclosed herein is the use of a compound of formula I, (Ia), or (Ib), or a pharmaceutically acceptable salt thereof, for the preparation of a medicament for use in therapy.

As used herein, "alkenyl" refers to both branched- and straight-chain unsaturated aliphatic hydrocarbon groups of 2 to 12 carbon atoms and having at least one carbon-carbon double bond. Alkenyl groups may be optionally substituted with one or more substituents as defined herein. Examples of such groups include, but are not limited to, ethenyl, propenyl, n-butenyl, 3-methylbut-2-enyl, n-pentenyl, octenyl and decenyl. "$C_{2-6}$alkenyl" refers to an alkenyl group as defined herein having 2 to 6 carbon atoms.

"Alkyl" refers to both branched- and straight-chain saturated aliphatic hydrocarbon groups of 1 to 18 carbon atoms, or more specifically, 1 to 12 carbon atoms. Examples of such groups include, but are not limited to, methyl (Me), ethyl (Et), n-propyl (Pr), n-butyl (Bu), n-pentyl, n-hexyl, and the isomers thereof such as isopropyl (i-Pr), isobutyl (i-Bu), sec-butyl (s-Bu), tert-butyl (t-Bu), isopentyl, and isohexyl. Alkyl groups may be optionally substituted with one or more substituents as defined herein. "$C_{1-6}$alkyl" refers to an alkyl group as defined herein having 1 to 6 carbon atoms.

"Aryl" refers to an aromatic monocyclic or multicyclic ring moiety comprising 6 to 14 ring carbon atoms, or more specifically, 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Halo" or "halogen" refers to fluoro, chloro, bromo or iodo, unless otherwise noted.

"Heterocycle" or "heterocyclyl" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

In one embodiment, partially unsaturated and aromatic 4-7 membered monocyclic heterocyclyl moieties include, but are not limited to, 2,3-dihydro-1,4-dioxinyl, dihydropyranyl, dihydropyrazinyl, dihydropyridazinyl, dihydropyridinyl, dihydropyrimidinyl, dihydrotriazolyl, furanyl, imidazolyl, isothiazolyl, isoxazolyl, oxadiazolyl, oxazolyl, oxoimidazolidinyl, pyranyl, pyrazinyl, pyrazolyl, pyridazinyl, pyridinyl, pyrimidinyl, pyrrolyl, tetrahydropyrazinyl, tetrahydropyridazinyl, tetrahydropyridinyl, tetrahydropyrimidinyl, tetrazolyl, thiadiazolyl, thiazolyl, thienyl, thiophenyl, and triazolyl.

In one embodiment, saturated 4-7 membered monocyclic heterocyclyl moieties include, but are not limited to, azetidinyl, 1,4-dioxanyl, hexahydroazepinyl, morpholinyl, 1,4-oxazepanyl, oxazolidinyl, oxetanyl, piperazinyl, piperidinyl, pyridin-2-onyl, pyrrolidinyl, tetrahydrofuranyl, tetrahydropyranyl, thiomorpholinyl, tetrahydrothienyl, and tetrahydrothiophenyl. In one embodiment, a saturated 4-7 membered monocyclic heterocyclyl is azetidinyl.

Heterocyclic groups may be optionally substituted with one or more substituents as defined herein.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions.

Polymorphism

A compound of formula (I), including a salt or solvate thereof, may exist in crystalline form, non-crystalline form, or a mixture thereof. A compound or a salt or solvate thereof may also exhibit polymorphism, i.e. the capacity of occurring in different crystalline forms. These different crystalline forms are typically known as "polymorphs". Polymorphs have the same chemical composition but differ in packing, geometrical arrangement, and other descriptive properties of crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, all of which may be used for identification. One of ordinary skill in the art will appreciate that different polymorphs may be produced, for example, by changing or adjusting the conditions used in crystallizing/recrystallizing a compound of formula (I).

Optical Isomers—Diastereomers—Geometric Isomers—Tautomers

Included herein are various isomers of the compounds of formula (I). The term "isomers" refers to compounds that have the same composition and molecular weight but differ in physical and/or chemical properties. The structural difference may be in constitution (geometric isomers) or in the ability to rotate the plane of polarized light (stereoisomers).

With regard to stereoisomers, a compound of formula (I) may have one or more asymmetric carbon atom and may occur as mixtures (such as a racemic mixture) or as individual enantiomers or diastereomers. All such isomeric forms are included herein, including mixtures thereof. If a compound of formula (I) contains a double bond, the substituent may be in the E or Z configuration. If a compound of formula (I) contains a disubstituted cycloalkyl, the cycloalkyl substituent may have a cis- or trans-configuration. All tautomeric forms are also intended to be included.

Any asymmetric atom (e.g., carbon) of a compound of formula (I), can be present in racemic mixture or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

A compound of formula (I), can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of the final compounds of the examples or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic compounds can also be resolved by chiral chromatography, e.g., high pressure liquid chromatography (HPLC) using a chiral adsorbent.

Some of the compounds described herein may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are included within the scope of the present invention.

Isotopic Variations

Compounds of formula (I), include unlabeled forms, as well as isotopically labeled forms. Isotopically labeled compounds have structures depicted by the formulas given herein except that one or more atoms are replaced by an atom having a selected atomic mass or mass number. Examples of isotopes that can be incorporated into compounds disclosed herein include isotopes of hydrogen, carbon, nitrogen, oxygen, phosphorous, sulfur, fluorine, iodine and chlorine, such as $^2H$ (i.e., Deuterium or "D"), $^3H$, $^{11}C$, $^{13}C$, $^{14}C$, $^{13}N$, $^{15}N$, $^{15}O$, $^{17}O$, $^{18}O$, $^{32}P$, $^{35}S$, $^{18}F$, $^{123}I$, $^{125}I$ and $^{36}Cl$. The invention includes various isotopically labeled compounds as defined herein, for example those into which radioactive isotopes, such as $^3H$ and $^{14}C$, or those into which non-radioactive isotopes, such as $^2H$ and $^{13}C$ are present. Such isotopically labeled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, substitution with positron emitting isotopes, such as $^{11}C$, $^{18}F$, $^{15}O$ and $^{13}N$, may be particularly desirable for PET or SPECT studies.

Isotopically-labeled compounds of formula (I), can generally be prepared by conventional techniques known to those skilled in the art. Furthermore, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index.

Pharmaceutically Acceptable Salts

The term "pharmaceutically acceptable salt" refers to a salt prepared from a pharmaceutically acceptable non-toxic base or acid, including inorganic or organic base and inorganic or organic acid. Salts derived from inorganic bases include aluminum, ammonium, calcium, copper, ferric, ferrous, lithium, magnesium, manganic salts, manganous, potassium, sodium, zinc, and the like. Particular embodiments include ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylene-diamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When a compound of formula (I), is basic, a salt may be prepared from a pharmaceutically acceptable non-toxic acid, including an inorganic and organic acid. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, trifluoroacetic acid (TFA) and the like. Particular embodiments include the citric, hydrobromic, hydrochloric, maleic, phosphoric, sulfuric, fumaric, tartaric and trifluoroacetic acids. It will be understood that, as used herein, references to the compounds disclosed herein are meant to also include pharmaceutically acceptable salts thereof.

Methods of Use

Compounds of the invention can inhibit activity of the enzyme indoleamine-2,3-dioxygenase (IDO). For example, the compounds disclosed herein can potentially be used to inhibit activity of IDO in cell or in an individual in need of modulation of the enzyme by administering an effective amount of a compound. Further disclosed herein are methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound or composition provided herein. Methods of measuring tryptophan levels and tryptophan degradation are routine in the art.

Also disclosed herein are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, viral replication, etc.

Also disclosed herein are methods of treating diseases associated with activity or expression, including abnormal activity and/or overexpression, of IDO in an individual (e.g., patient) by administering to the individual in need of such treatment an effective amount or dose of a compound disclosed herein or a pharmaceutical composition thereof. Example diseases can include any disease, disorder or condition that may be directly or indirectly linked to expression or activity of the IDO enzyme, such as over expression or abnormal activity. An IDO-associated disease can also include any disease, disorder or condition that may be prevented, ameliorated, or cured by modulating enzyme activity. Examples of IDO-associated diseases include cancer, viral infection such as HIV and HCV, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosusor. Example cancers potentially treatable by the methods herein include cancer of the colon, pancreas, breast, prostate, lung, brain, ovary, cervix, testes, renal, head and neck, lymphoma, leukemia, melanoma, and the like. The compounds of the invention may also be useful in the treatment of obesity and ischemia. As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound disclosed herein includes the administration of a compound of the present invention to an individual or patient, such as a human, as well as, for example, introducing a compound of the invention into a sample containing a cellular or purified preparation containing the IDO enzyme.

A subject administered with a compound disclosed herein, or a pharmaceutically acceptable salt thereof, is generally a mammal, such as a human being, male or female. A subject also refers to cows, sheep, goats, horses, dogs, cats, rabbits, rats, mice, fish, and birds. In one embodiment, the subject is a human.

As used herein, the terms "treatment" and "treating" refer to all processes wherein there may be a slowing, interrupting, arresting, controlling, or stopping of the progression of a disease or disorder that may be associated with IDO enzyme activity. The terms do not necessarily indicate a total elimination of all disease or disorder symptoms. The terms also include the potential prophylactic therapy of the mentioned conditions, particularly in a subject that is predisposed to such disease or disorder.

The terms "administration of" and or "administering a" compound should be understood to include providing a compound described herein, or a pharmaceutically acceptable salt thereof, and compositions of the foregoing to a subject.

The amount of a compound administered to a subject is an amount sufficient to inhibit IDO enzyme activity in the subject. In an embodiment, the amount of a compound can be an "effective amount", wherein the subject compound is administered in an amount that will elicit a biological or medical response of a tissue, system, animal or human that is being sought by a researcher, veterinarian, medical doctor or other clinician. An effective amount does not necessarily include considerations of toxicity and safety related to the administration of a compound. It is recognized that one skilled in the art may affect physiological disorders associated with an IDO enzyme activity by treating a subject presently afflicted with the disorders, or by prophylactically treating a subject likely to be afflicted with the disorders, with an effective amount of a compound disclosed herein, or a pharmaceutically acceptable salt thereof.

An effective amount of a compound will vary with the particular compound chosen (e.g. considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen. Typical daily dosages for oral administration, to a human weighing approximately 70 kg would range from about 0.1 mg to about 2 grams, or more specifically, 0.1 mg to 500 mg, or even more specifically, 0.2 mg to 100 mg, of a compound of formula (I).

One embodiment of the present invention provides for a method of treating a disease or disorder associated with IDO enzyme activity comprising administration of an effective amount of a compound of formula (I) to a subject in need of treatment thereof. In one embodiment, the disease or disorder associated with an IDO enzyme is a cell proliferation disorder.

In one embodiment, disclosed herein is the use of a compound of formula (I) in a therapy. The compound may be useful in a method of inhibiting IDO enzyme activity in a subject, such as a mammal in need of such inhibition, comprising administering an effective amount of the compound to the subject.

In one embodiment, disclosed herein is a pharmaceutical composition comprising a compound of formula (I), or a pharmaceutically acceptable salt thereof, for use in potential treatment of a disorder or disease related to IDO enzyme activity.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of formula I, (Ia), or (Ib), or a pharmaceutically acceptable salt thereof, and one or more pharmaceutically acceptable carriers or excipients. Accordingly, the compositions of the present invention encompass any composition made by admixing a compound of the present invention and one or more pharmaceutically acceptable carrier or excipients. By "pharmaceutically acceptable" it is meant the carriers or excipients are compatible with the compound disclosed herein and with other ingredients of the composition.

In one embodiment, disclosed herein is a composition comprising a compound of formula (I), or a pharmaceutically acceptable salt thereof, and one or more pharmaceutically acceptable carriers or excipients. The composition may be prepared and packaged in bulk form wherein an effective amount of a compound of the invention can be extracted and then given to a subject, such as with powders or syrups. Alternatively, the composition may be prepared and packaged in unit dosage form wherein each physically discrete unit contains an effective amount of a compound of formula (I). When prepared in unit dosage form, the composition of the invention typically contains from about 0.1 mg to 2 grams, or more specifically, 0.1 mg to 500 mg, or even more specifically, 0.2 mg to 100 mg, of a compound of formula (I), or a pharmaceutically acceptable salt thereof.

A compound disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the invention. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the invention are prepared using techniques and methods known to those skilled in the art. Some methods commonly used in the art are described in Remington's Pharmaceutical Sciences (Mack Publishing Company).

In one embodiment, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives, (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch) gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example polylactic acid, poly epsilon caprolactone, polyhydroxy butyric acid, polyorthoesters, polyacetals, polydihydropyrans, polycyanacrylates and cross-linked or amphipathic block copolymers of hydrogels.

In one embodiment, the invention is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the invention in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the invention is directed to compositions for parenteral administration. Compositions adapted for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

A compound disclosed herein may be used in combination with one or more other active agents, including but not limited to, other anti-cancer agents, that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present invention.

When a compound disclosed herein is used contemporaneously with one or more other active agents, a composition containing such other active agents in addition to the compound disclosed herein is contemplated. Accordingly, the compositions of the present invention include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a compound of formula (I) and one or more other active agent(s) together in the same pharmaceutical composition, or a compound of formula (I), and one or more other therapeutic agent(s) in separate form, e.g. in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, the invention provides a composition comprising a compound of formula (I), and at least one other therapeutic agent as a combined preparation for simultaneous, separate or sequential use in therapy. In one embodiment, the therapy is the treatment of a disease or disorder associated with IDO enzyme activity.

In one embodiment, the invention provides a kit comprising two or more separate pharmaceutical compositions, at least one of which contains a compound of formula (I). In one embodiment, the kit comprises means for separately retaining said compositions, such as a container, divided bottle, or divided foil packet. An example of such a kit is a blister pack, as typically used for the packaging of tablets, capsules and the like.

A kit disclosed herein may be used for administering different dosage forms, for example, oral and parenteral, for administering the separate compositions at different dosage intervals, or for titrating the separate compositions against one another. To assist with compliance, a kit of the invention typically comprises directions for administration.

Disclosed herein is a use of a compound of formula (I), for treating a disease or disorder associated with IDO enzyme activity, wherein the medicament is prepared for administration with another active agent. The invention also provides the use of another active agent for treating a disease or disorder associated with an IDO enzyme, wherein the medicament is administered with a compound of formula (I).

The invention also provides the use of a compound of formula (I) for treating a disease or disorder associated with IDO enzyme activity, wherein the patient has previously (e.g. within 24 hours) been treated with another active agent. The invention also provides the use of another therapeutic agent for treating a disease or disorder associated with IDO enzyme activity, wherein the patient has previously (e.g. within 24 hours) been treated with a compound of formula I, (Ia), or (Ib). The second agent may be applied a week, several weeks, a month, or several months after the administration of a compound disclosed herein.

In one embodiment, the other active agent is selected from the group consisting of vascular endothelial growth factor (VEGF) receptor inhibitors, topoisomerase II inhibitors, smoothen inhibitors, alkylating agents, anti-tumor antibiotics, anti-metabolites, retinoids, immunomodulatory agents including but not limited to anti-cancer vaccines, CTLA-4, LAG-3 and PD-1 antagonists.

Examples of vascular endothelial growth factor (VEGF) receptor inhibitors include, but are not limited to, bevacizumab (sold under the trademark AVASTIN by Genentech/Roche), axitinib, (N-methyl-2-[[3-[([pound])-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indoi-6-yl)-2-[(4-pyridinyimethyj)amino]-3-pyridinecarboxamide, and described in PCT Publication No. WO 02/068470), pasireotide (also known as SO 230, and described in PCT Publication No. WO 02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX and MYLERAN), carboplatin (sold under the tradename PARAPLATIN), lomustine (also known as CCNU, sold under the tradename CeeNU), cisplatin (also known as CDDP, sold under the tradenames PLATINOL and PLATINOL-AQ), chlorambucil (sold under the tradename LEUKERAN), cyclophosphamide (sold under the tradenames CYTOXAN and NEOSAR), dacarbazine (also known as DTIC, DIC and imidazole carboxamide, sold under the tradename DTIC-DOME), altretamine (also known as hexamethylmelamine (HMM) sold under the tradename HEXALEN), ifosfamide (sold under the tradename IFEX), procarbazine (sold under the tradename MATULANE), mechlorethamine (also known as nitrogen mustard, mustine and mechloroethamine hydrochloride, sold under the tradename MUSTARGEN), streptozocin (sold under the tradename ZANOSAR), thiotepa (also known as thiophosphoamide, TESPA and TSPA, and sold under the tradename THIOPLEX).

Examples of anti-tumor antibiotics include, but are not limited to, doxorubicin (sold under the tradenames ADRIAMYCIN and RUBEX), bleomycin (sold under the tradename LENOXANE), daunorubicin (also known as dauorubicin hydrochloride, daunomycin, and rubidomycin hydrochloride, sold under the tradename CERUBIDINE), daunorubicin liposomal (daunorubicin citrate liposome, sold under the tradename DAUNOXOME), mitoxantrone (also known as DHAD, sold under the tradename NOVANTRONE), epirubicin (sold under the tradename ELLENCE), idarubicin (sold under the tradenames IDAMYCIN, IDAMYCIN PFS), and mitomycin C (sold under the tradename MUTAMYCIN).

Examples of anti-metabolites include, but are not limited to, claribine (2-chlorodeoxyadenosine, sold under the tradename LEUSTATIN), 5-fluorouracil (sold under the tradename ADRUCIL), 6-thioguanine (sold under the tradename PURINETHOL), pemetrexed (sold under the tradename ALIMTA), cytarabine (also known as arabinosylcytosine (Ara-C), sold under the tradename CYTOSAR-U), cytarabine liposomal (also known as Liposomal Ara-C, sold under the tradename DEPOCYT), decitabine (sold under the tradename DACOGEN), hydroxyurea (sold under the tradenames HYDREA, DROXIA and MYLOCEL), fludarabine (sold under the tradename FLUDARA), floxuridine (sold under the tradename FUDR), cladribine (also known as 2-chlorodeoxyadenosine (2-CdA) sold under the tradename LEUSTATIN), methotrexate (also known as amethopterin, methotrexate sodium (MTX), sold under the tradenames RHEUMATREX and TREXALL), and pentostatin (sold under the tradename NIPENT).

Examples of retinoids include, but are not limited to, alitretinoin (sold under the tradename PANRETIN), tretinoin (all-trans retinoic acid, also known as ATRA, sold under the tradename VESANOID), Isotretinoin (13-c/s- retinoic acid, sold under the tradenames ACCUTANE, AMNESTEEM, CLARAVIS, CLARUS, DECUTAN, ISOTANE, IZOTECH, ORATANE, ISOTRET, and SOTRET), and bexarotene (sold under the tradename TARGRETIN).

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDL1, B7H1, B7-4, CD274 and B7-H for PD-L; and PDCD1L2, PDL2, B7-DC, Btdc and CD273 for PD-L2. In any of the treatment method, medicaments and uses of the present invention in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present invention include a monoclonal antibody (mAb), or antigen binding fragment thereof, which specifically binds to PD-1 or PD-L1, and preferably specifically binds to human PD-1 or human PD-L. The mAb may be a human antibody, a humanized antibody or a chimeric antibody, and may include a human constant region. In some embodiments the human constant region is selected from the group consisting of IgG1, IgG2, IgG3 and IgG4 constant regions, and in preferred embodiments, the human constant region is an IgG or IgG4 constant region. In some embodiments, the antigen binding fragment is selected from the group consisting of Fab, Fab'-SH, F(ab')$_2$, scFv and Fv fragments. Examples of PD-1 antagonists include, but are not limited to, pembrolizumab (sold under the tradename KEYTRUDA) and nivolumab (sold under the tradename OPDIVO).

Examples of mAbs that bind to human PD-1, and useful in the treatment method, medicaments and uses of the present invention, are described in U.S. Pat. Nos. 7,488,802, 7,521,051, 8,008,449, 8,354,509, 8,168,757, WO2004/004771, WO2004/072286, WO2004/056875, and US2011/0271358.

Examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C and an antibody which comprises the heavy chain and light chain variable regions of SEQ ID NO:24 and SEQ ID NO:21, respectively, of WO2013/019906.

Other PD-1 antagonists useful in any of the treatment method, medicaments and uses of the present invention include an immunoadhesin that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Examples of other cytotoxic agents include, but are not limited to, arsenic trioxide (sold under the tradename TRISENOX), asparaginase (also known as L-asparaginase, and Erwinia L-asparaginase, sold under the tradenames ELSPAR and KIDROLASE).

EXPERIMENTAL

The following examples are intended to be illustrative only and not limiting in any way. Abbreviations used are those conventional in the art or the following.
ACN acetonitrile
° C. degree Celsius
DCM dichloromethane
DMA dimethylamine
DMF N,N-dimethylformamide
DMSO dimethylsulfoxide
EtOAc ethyl acetate
EtOH ethanol
g gram
h hour(s)
HPLC high pressure liquid chromatography
kg kilogram
L liter
LC liquid chromatography
LCMS liquid chromatography and mass spectrometry
MeOH methanol
MS mass spectrometry
MTBE methyl tert-butyl ether
min minutes
mL milliliter(s)
m/z mass to charge ratio
nm nanometer
nM nanomolar
N normal
MR nuclear magnetic resonance
RT or rt room temperature
sat. saturated
TEA triethyl amine
FA trifluoroacetic acid
THF tetrahydrofuran

INTERMEDIATES

Intermediate A: 4-Amino-N'-hydroxy-1,2,5-oxadiazole-3-carboximidamide

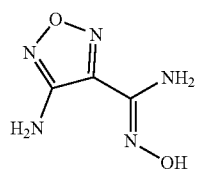

Malononitrile (15 g, 227 mmol) in 2N HCl (200 mL) was stirred till dissolved. With the reaction temperature kept between 15° C.-20° C., a solution of sodium nitrite (31.3 g, 454 mmol) in 45 mL of water was added dropwise and stirred at ambient for a further 16 h. An aqueous solution of hydroxylamine hydrochloride (35.0 g, 504 mmol) in 25 mL of water was added and the pH of the solution was brought to about 10 by addition of 10 N NaOH while maintaining the temperature below 20° C. The temperature of the reaction was brought to 30° C. for 1 h then refluxed for 3 h. Heating was discontinued and the reaction gradually cooled to RT overnight. The reaction was cooled in an ice bath, pH adjusted to 8 with 6N HCl and stirred for 30 min. The solids were filtered and washed with cold water to afford the title compound. MS: 144 (M+1). $^{13}$C NMR (500 MHz, CD$_3$OD): δ 154.5, 144.3, 139.8.

Intermediate B:
4-Amino-N-hydroxy-1,2,5-oxadiazole-3-carbimidoyl chloride

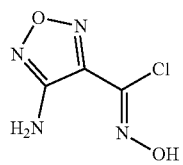

To a solution of 4-amino-N'-hydroxy-1,2,5-oxadiazole-3-carboximidamide (5.09 g, 35.6 mmol) in 70 mL of water was added AcOH (35 mL) and 6N hydrogen chloride (17.78 mL, 107 mmol). The reaction mixture was warmed to 40° C. till all solids were dissolved. The reaction was cooled to ambient and solid sodium chloride (6.24 g, 107 mmol) was added, stirred, then the reaction mixture was cooled to 0° C. A solution of sodium nitrite (2.5 g, 35.6 mmol) in 8.4 mL of water was added dropwise over 3 h and the reaction was stirred at 0° C. for a further 1.5 h, then warmed to 15° C. for 15 min. The solid precipitates were filtered and washed with cold water to afford the title product. MS: 163 (M+1). $^{13}$C NMR (500 MHz, DMSO-d$_6$): δ 154.4, 142.3, 126.8. $^1$HNMR (500 MHz, DMSO-d$_6$): δ 13.41 (s, 1H), 6.29 (s, 2H).

Intermediate C: 4-Fluorobicyclo[4.2.0]octa-(6),2,4-trien-7-amine hydrochloride

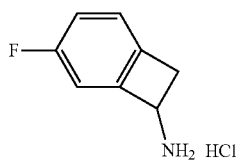

Step 1: 3-(2-bromo-4-fluorophenyl)acrylonitrile

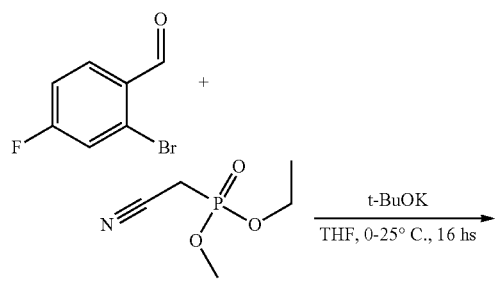

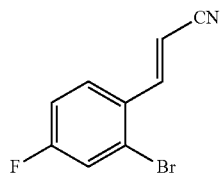

To a solution of 2-bromo-4-fluorobenzaldehyde (400.0 g, 1.97 mol) and diethyl (cyanomethyl)phosphonate (401.0 g, 2.266 mol) in THF (7 L) was added potassium 2-methyl-propan-2-olate (254 g, 2.266 mol) portion-wise at 0° C. After 16 h at 25° C., water (2.5 L) was added and the mixture was stirred for another 10 min. Layers were separated. The aqueous layer was extracted with ethyl acetate (1.5 L×3). The combined organic layers were washed with brine (2.0 L), dried over anhydrous Na$_2$SO$_4$, filtered, and concentrated in vacuo. The residue was purified by column chromatography on silica gel (SiO$_2$, eluting with petroleum) to give the title compound.

Step 2: 3-(2-bromo-4-fluorophenyl)propanenitrile

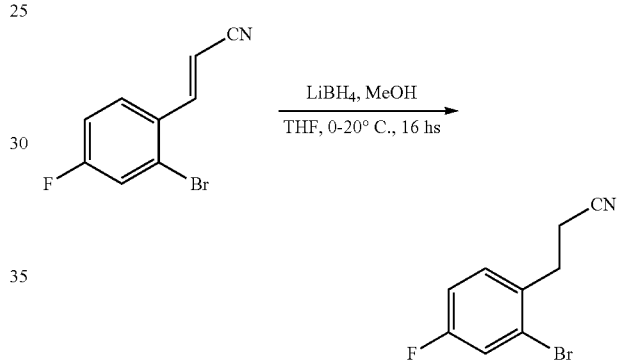

To a solution of 3-(2-bromo-4-fluorophenyl)acrylonitrile (160.0 g, 708 mmol) in THF (1.5 L) was added LiBH$_4$ (30.0 g, 1377 mmol) at 0° C. in portions over 5 min. The mixture was stirred at the 0° C. for 30 min, followed by the addition of methanol (20 mL) dropwise, warmed to 20° C., and stirred for 16 h. The mixture was quenched by adding 2.0 M KH$_2$PO$_4$ aqueous solution until pH~7, extracted with ethyl acetate (500 mL×2). The organic layers were washed with brine (sat. 100 mL), dried over anhydrous sodium sulfate, filtered, and concentrated under reduce pressure. The residue was purified by column chromatography on silica gel (SiO$_2$, eluting with petroleum ether/ethyl acetate=50:1 to 30:1) to give the title compound as an oil. $^1$H NMR (400 MHz, CDCl$_3$) δ 7.28-7.40 (m, 2H), 7.04 (td, J=8.0, 2.8 Hz, 1H), 3.07 (t, J=7.2 Hz, 2H), 2.67 (t, J=7.2 Hz, 2H).

Step 3: 4-fluorobicyclo[4.2.0]octa-1,3,5-triene-7-carbonitrile

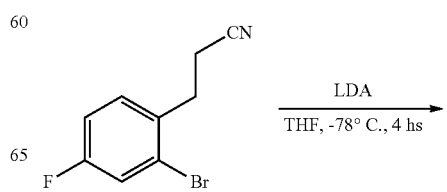

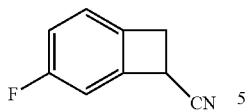

To a stirred solution of diisopropylamine (0.222 L, 1579 mmol) in THF (1.5 L) was added n-BuLi (0.631 L, 1579 mmol) (2.5 M, in hexane) dropwise at −78° C. under $N_2$ atmosphere. After the addition was finished, the reaction was stirred at −78° C. for 30 min before 3-(2-bromo-4-fluorophenyl)propanenitrile (90.0 g, 395 mmol) in THF (500 mL) was added dropwise under $N_2$ atmosphere. The mixture was stirred at −78° C. for 3 h, warmed to RT, quenched with aq. HCl (1.7 L, 1 M) to pH~8, extracted by ethyl acetate (500 mL×2). The organic layers were washed with brine (200 mL), dried over $Na_2SO_4$, filtered, and concentrated under reduce pressure. The residue was purified by column chromatography on silica gel ($SiO_2$, eluting with petroleum ether/ethyl acetate=50:1 to 30:1) to give title compound as an oil. $^1$H NMR (400 MHz, $CDCl_3$) δ 7.04-7.16 (m, 2H), 6.92-7.00 (m, 1H), 4.21-4.25 (m, 1H), 3.62-3.68 (m, 1H), 3.45-3.53 (m, 1H)

Step 4: 4-Fluorobicyclo[4.2.0]octa-1,3,5-triene-7-carboxylic acid

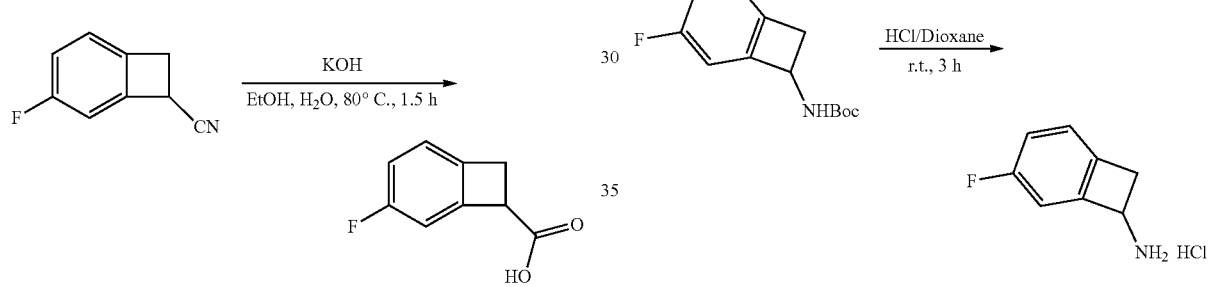

To a stirred solution of 4-fluorobicyclo[4.2.0]octa-1,3,5-triene-7-carbonitrile (73.0 g, 496 mmol) in EtOH (700 mL) and water (140 mL) was added potassium hydroxide (97.0 g, 1736 mmol) at 25° C. After the addition was finished, the reaction mixture was stirred at 80° C. for 1.5 h, cooled to RT, and concentrated under reduced pressure. The residue was dissolved in water (500 mL) and extracted by DCM (300 mL). The aqueous phase was acidified by adding aqueous HCl (6M) to a pH value of ~3, then extracted by ethyl acetate (800 mL×2). The organic layers were washed with brine (400 mL), dried over $Na_2SO_4$, filtered, and concentrated in vacuo to give the title compound as a solid. $^1$H NMR (400 MHz, $CDCl_3$) δ 7.04-7.07 (m, 1H), 6.92-6.97 (m, 2H), 4.30 (t, J=4.0 Hz, 1H), 3.43-3.45 (m, 2H).

Step 5: tert-Butyl (4-fluorobicyclo[4.2.0]octa-1(6),2,4-trien-7-yl)carbamate

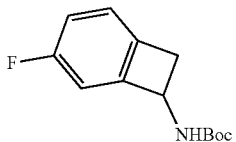

To a stirred solution of 4-fluorobicyclo[4.2.0]octa-1,3,5-triene-7-carboxylic acid (26.0 g, 156 mmol) in t-BuOH (100 mL) were added triethylamine (32.7 mL, 235 mmol) and diphenyl phosphorazidate (51.7 g, 188 mmol). The mixture was stirred at 85° C. for 4 h under $N_2$ atmosphere, cooled to RT, and concentrated under reduced pressure. The residue was purified by silica chromatography (petroleum ether/ethyl acetate=50: 1-30:1) to afford the title compound. $^1$H NMR (400 MHz, $CD_3OD$) δ 7.07-7.14 (m, 1H), 6.96-7.03 (m, 1H), 6.94 (dd, J=7.9, 2.2 Hz, 1H), 5.07 (br s, 1H), 3.54 (br dd, J=14.1, 4.4 Hz, 1H), 2.97 (br d, J=14.1 Hz, 1H), 1.49 (s, 9H).

Step 6: 4-Fluorobicyclo[4.2.0]octa-(6),2,4-trien-7-amine hydrochloride

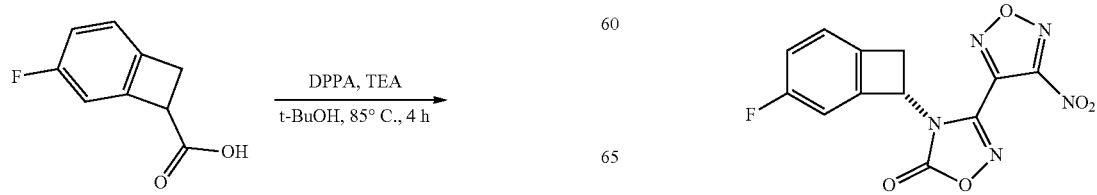

To a solution of tert-butyl (4-fluorobicyclo[4.2.0]octa-1,3,5-trien-7-yl)carbamate (25 g, 105 mmol) in EtOAc (200 mL) was added HCl (100 mL, 400 mmol) (4 M in dioxane) at RT. The mixture was stirred for 2 h at RT (~26° C.). LCMS and TLC (petroleum ether: ethyl acetate=5:1) showed no starting material. The precipitate was collected by filtration to give 4-fluorobicyclo[4.2.0]octa-1,3,5-trien-7-amine hydrochloride (16.0 g, 92 mmol) as a solid. ESI MS m/z 138.1 [M+H+]. $^1$H NMR (400 MHz, $CD_3OD$) δ 7.24-7.30 (m, 1H), 7.15-7.22 (m, 1H), 7.12 (dd, J=7.5, 2.2 Hz, 1H), 4.79-4.84 (m, 1H), 3.63-3.71 (m, 1H), 3.24 (br d, J=14.5 Hz, 1H).

Intermediates D and E: (S)- and (R)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one

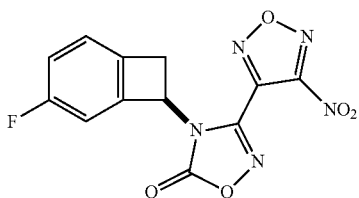

Step 1: 4-amino-N-(4-fluorobicyclo[4.2.0]octa-(6),2,4-trien-7-yl)-N'-hydroxy-1,2,5-oxadiazole-3-carboximidamide

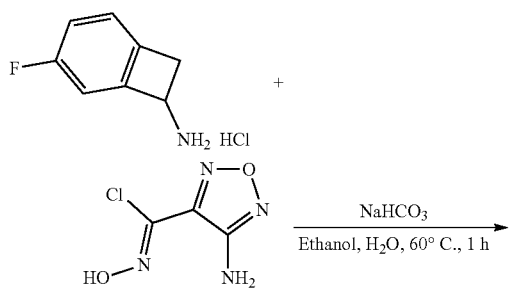

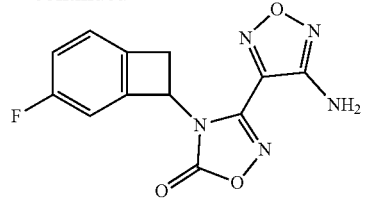

To a solution of 4-amino-N-(4-fluorobicyclo[4.2.0]octa-1(6),2,4-trien-7-yl)-N'-hydroxy-1,2,5-oxadiazole-3-carboximidamide (18.0 g, 68.4 mmol) and CDI (11.09 g, 68.4 mmol) in THF (180 ml) was added Et₃N (19.06 ml, 137 mmol). The reaction mixture was stirred at 26° C. for 2 h under N₂ atmosphere (balloon), then concentrated under reduced pressure. The residue was partitioned between water (300 mL) and DCM (300 mL). The aqueous layer was extracted with DCM (300 mL*2). The combined organic layers were washed with brine (300 mL), dried over Na₂SO₄, filtered, and concentrated under reduced pressure. The residue was purified by column chromatography (SiO₂, Pet. ether/ethyl acetate 10:1-3:1 as eluent) to give the title compound (16.5 g, 57.0 mmol) as a solid.

Step 3: 4-(4-fluorobicyclo[4.2.0]octa-1(6),2,4-trien-7-yl)-3-(4-nitro-1,2,5-oxadiazol-3-yl)-1,2,4-oxadiazol-5(4H)-one

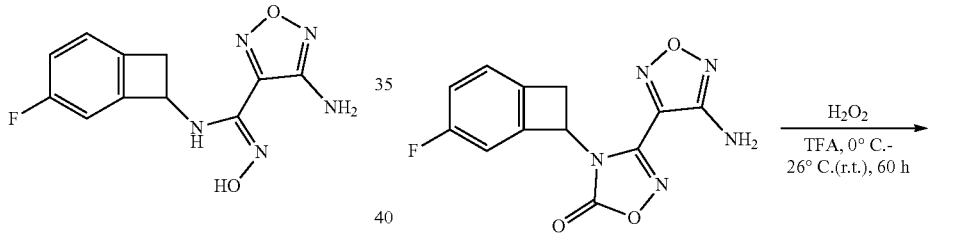

To a solution of 4-fluorobicyclo[4.2.0]octa-1,3,5-trien-7-amine hydrochloride (15 g, 86 mmol) in EtOH (150 mL) were added 4-amino-N-hydroxy-1,2,5-oxadiazole-3-carbimidoyl chloride (16.85 g, 104 mmol) and sodium hydrogencarbonate (18.15 g, 216 mmol). The mixture was stirred at 60° C. for 1 h, cooled to RT, and concentrated in vacuo. The residue was purified by silica chromatography (SiO₂, petroleum ether/AcOEt: 10:1 to 4:1) to afford the title compound (18.0 g, 68.4 mmol) as a solid. LC/MS: MS (ESI) m/z: 264.1 [M+H⁺].

Step 2: 3-(4-amino-1,2,5-oxadiazol-3-yl)-4-(4-fluorobicyclo[4.2.0]octa-1(6),2,4-trien-7-yl)-1,2,4-oxadiazol-5(4H)-one

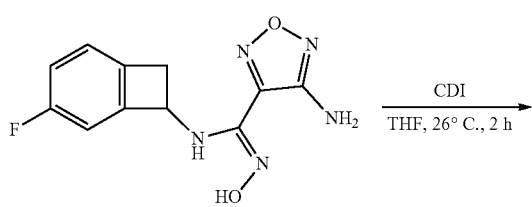

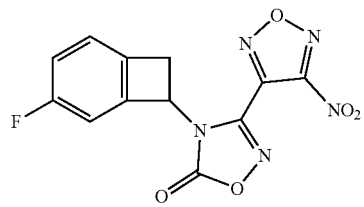

To a stirred solution of 3-(4-amino-1,2,5-oxadiazol-3-yl)-4-(4-fluorobicyclo[4.2.0]octa-1,3,5-trien-7-yl)-1,2,4-oxadiazol-5(4H)-one (15 g, 51.9 mmol) in TFA (1000 mL) was added hydrogen peroxide (174 mL, 51.9 mmol, 30%) at 0° C. The reaction was stirred at 15° C. for 15 h, extracted with DCM (1500 mL*8). The organic layers were washed with brine (200 ml*3), dried over Na₂SO₄, filtered, and concentrated in vacuo to give the title compound (70.2% yield) as a solid. ¹H NMR (400 MHz, CD₃Cl) δ 7.05 (br d, J=6.6 Hz, 2H), 6.73 (br d, J=6.8 Hz, 1H), 5.65 (br d, J=3.1 Hz, 1H), 3.79 (dd, J=1.5, 5.0, 14.7 Hz, 1H), 3.41 (br d, J=14.8 Hz, 1H)

Step 4: (S)- and (R)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one

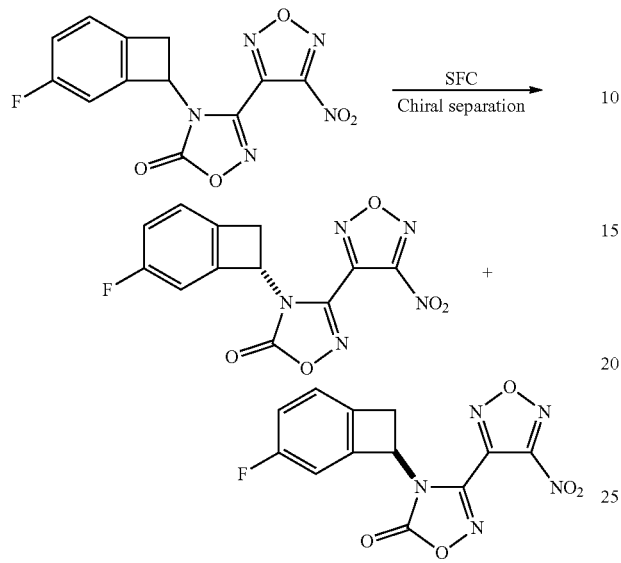

The above racemic compound was submitted to SFC chiral separation (Column OD 250 mm*50 mm, 10 um; Mobile phase: A: $CO_2$ B: ethanol; Gradient: 15% B; Flow rate: 180 ml/min). The two chiral intermediates F and G were obtained as solids:

Intermediate F (peak 1): $^1$H NMR (400 MHz, $CD_3Cl$) δ 7.05 (br d, J=6.6 Hz, 2H), 6.73 (br d, J=6.8 Hz, 1H), 5.65 (br d, J=3.1 Hz, 1H), 3.79 (ddd, J=1.5, 5.0, 14.7 Hz, 1H), 3.41 (br d, J=14.8 Hz, 1H)

Intermediate G (peak 2): $^1$H NMR (400 MHz, $CD_3Cl$) δ 7.05 (br d, J=6.6 Hz, 2H), 6.73 (br d, J=6.8 Hz, 1H), 5.65 (br d, J=3.1 Hz, 1H), 3.79 (ddd, J=1.5, 5.0, 14.7 Hz, 1H), 3.41 (br d, J=14.8 Hz, 1H)

General Synthetic Schemes

The compounds of formula I, (Ia), or (Ib) may be prepared by methods known in the art of organic synthesis as set forth in part by the following synthetic schemes and synthetic procedures and conditions for the illustrative intermediates and examples.

In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art.

The compounds described herein may be made from commercially available starting materials or synthesized using known organic, inorganic, and/or enzymatic processes. Exemplary synthetic schemes are described below.

Scheme 1.

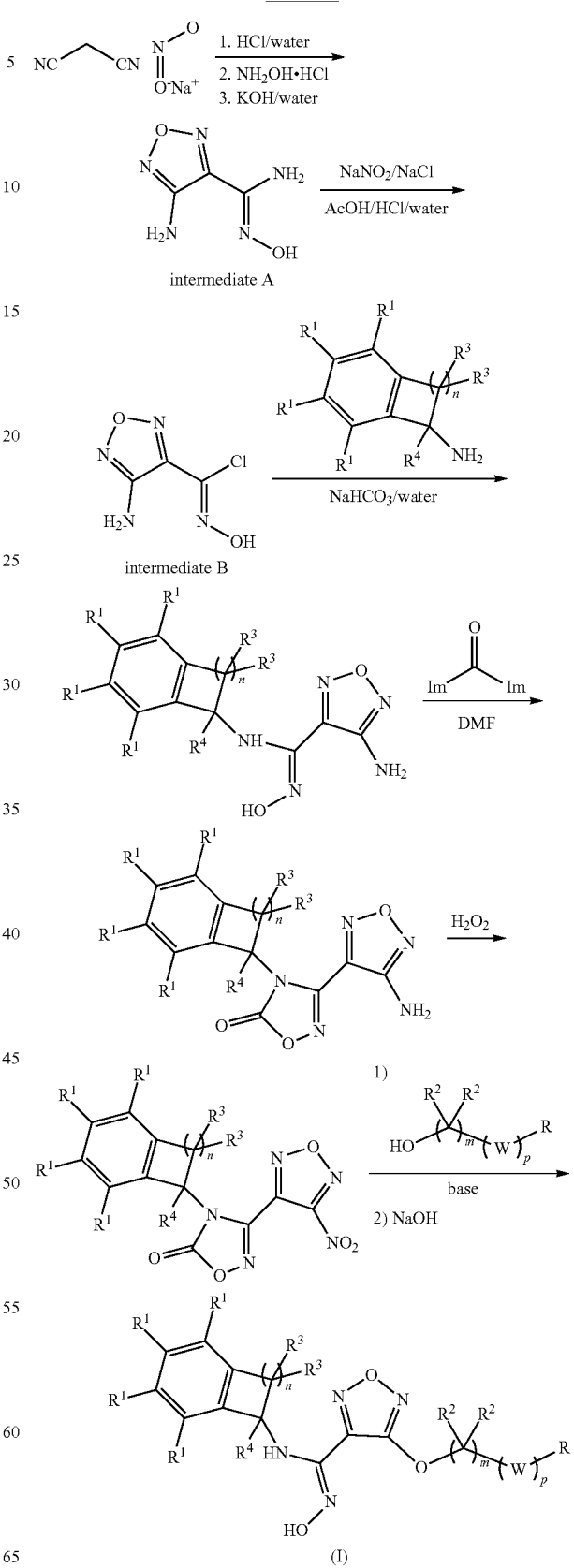

In Scheme 1, processes for preparing compounds, for example those in Examples 1-4, are described in more detail below in the Examples section.

EXAMPLES

Example 1. (S)—N-(4-fluorobicyclo[4.2.0]octa-1(6),2,4-trien-7-yl)-N'-hydroxy-4-(2-(sulfamoylamino)ethoxy)-1,2,5-oxadiazole-3-carboximidamide

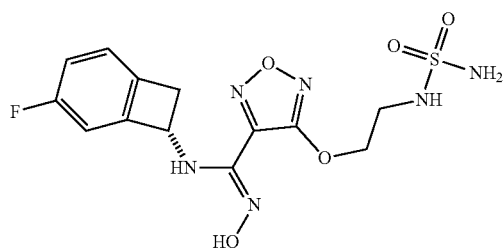 [SMILES: NS(=O)(=O)NCCOc1nonc1/C(=N/O)N[C@H]1Cc2ccc(F)cc21]

Step 1. 2-((tert-butyldiphenylsilyl)oxy)ethanamine

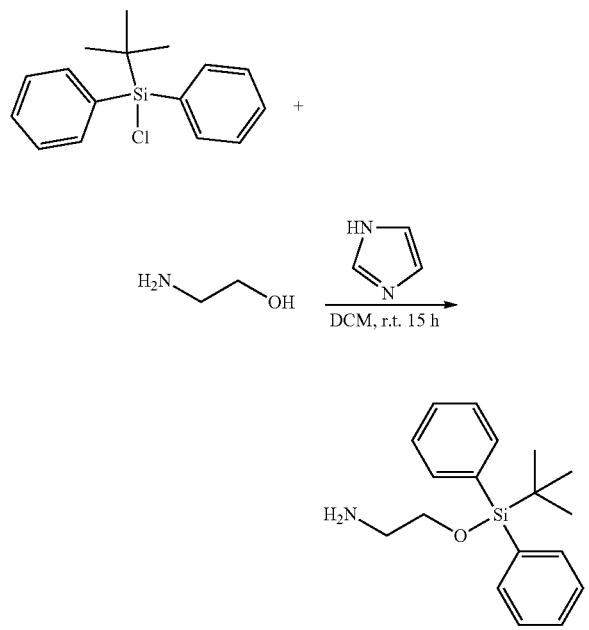

To a stirred solution of 2-aminoethanol (20.0 g, 327 mmol) and TBDPSCl (100 g, 362 mmol) in DCM (800 mL) was added 1H-imidazole (49 g, 720 mmol) at 0° C. The reaction was stirred at 10° C. for 15 h, diluted with water (400 mL), extracted with DCM (500 mL*2). The organic layers were washed with brine, dried over $Na_2SO_4$, filtered, and concentrated in vacuo. The residue was purified by silica gel chromatography ($SiO_2$, pet. ether/EtOAc 20:1-10:1-5:1) to give 2-((tert-butyldiphenylsilyl)oxy)ethanamine (52 g) as an oil. $^1$H NMR (400 MHz, $CDCl_3$) δ 7.68 (dd, J=7.8, 1.6 Hz, 4H), 7.3-7.5 (m, 6H), 3.6-3.7 (m, 2H), 2.8 (t, J=5.2 Hz, 2H) 1.1 (s, 9H); ESI MS m/z=300.1

Step 2. tert-Butyl N-(2-((tert-butyldiphenylsilyl)oxy)ethyl)sulfamoylcarbamate

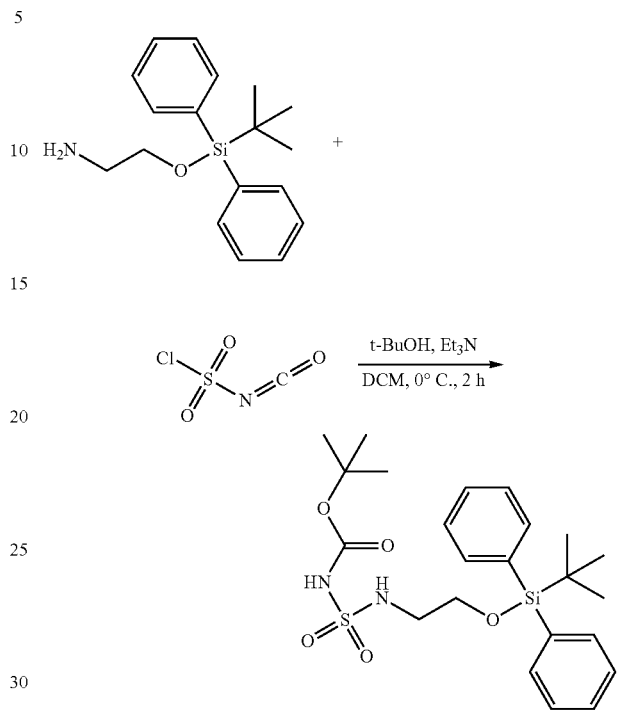

To a solution of sulfurisocyanatidic chloride (6.14 g, 43.4 mmol) in DCM (100 mL) was added a solution of t-BuOH (3.22 g, 43.4 mmol) in DCM (50 mL) slowly at 0° C. The reaction was stirred at 0° C. for 30 min before 2-((tert-butyldiphenylsilyl)oxy)ethanamine (10 g, 33.4 mmol) was added in small portions to keep the internal temperature below 10° C. The reaction was stirred at 0° C. for another 5 min before TEA (10.4 mL, 74.6 mmol) was added slowly to keep the internal temperature below 10° C. The reaction was stirred at 0° C. for 2 h, quenched by saturated aqueous $NH_4Cl$ solution (100 mL), then extracted by DCM (250 mL*3). The organic layers were washed with brine (100 mL), dried over $Na_2SO_4$, filtered, and concentrated in vacuo. The residue was purified by silica gel chromatography ($SiO_2$, petroleum ether/ethyl acetate=100% to 50%) to give tert-butyl N-(2-((tert-butyldiphenylsilyl)oxy)ethyl)sulfamoylcarbamate (7.5 g) as a solid. $^1$H NMR (400 MHz, $CD_3OD$) δ 7.67 (dd, J=1.5, 7.7 Hz, 4H), 7.45-7.37 (m, 6H), 3.76 (t, J=6.2 Hz, 2H), 3.17 (t, J=6.2 Hz, 2H), 1.44 (s, 9H), 1.04 (s, 9H)

Step 3. tert-Butyl N-(2-hydroxyethyl)sulfamoylcarbamate

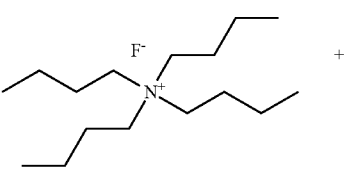

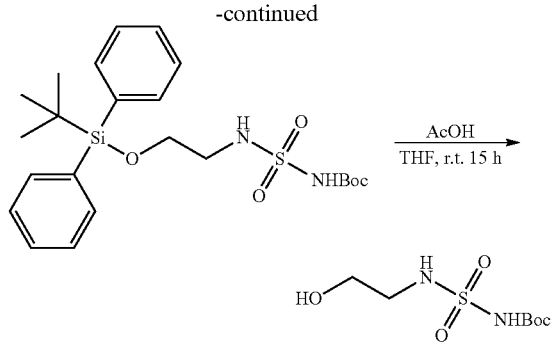

To a stirred solution of tert-butyl N-(2-((tert-butyldiphenylsilyl)oxy)ethyl)sulfamoylcarbamate (7.5 g, 15.67 mmol) in THF (35 mL) under an argon atmosphere was added acetic acid (9.41 g, 157 mmol) at 0° C., followed by a solution of tetrabutylammonium fluoride in THF (1.0 M, 22 mL, 22.0 mmol) drop-wise. After the addition, the reaction was stirred at 10° C. for 15 h, quenched with saturated NH₄Cl solution (50 mL), then extracted by EtOAc (150 mL*2). The organic layers were washed with brine, dried over Na₂SO₄, filtered, and concentrated in vacuo. The residue was purified by silica gel chromatography (SiO₂, petroleum ether/EtOAc 100% to 50%) to give tert-butyl N-(2-hydroxyethyl)sulfamoylcarbamate (2.81 g) as a solid. ¹H NMR (400 MHz, CD₃OD) δ 3.63 (t, J=6.0 Hz, 2H), 3.10 (t, J=6.0 Hz, 2H), 1.49 (s, 9H).

Step 4. N-(2-hydroxyethyl)sulfamide

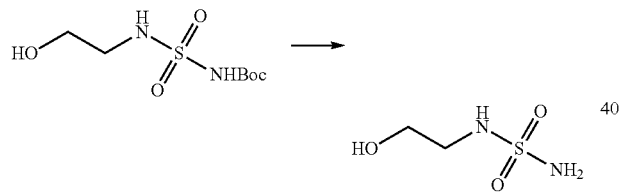

Tert-Butyl N-(2-hydroxyethyl)sulfamoylcarbamate (500 mg, 2.08 mmol) was dissolved in HCl-methanol solution (5 mL, 4.0 M, 20.00 mmol). The reaction was stirred at 10° C. for 2 h, then concentrated in vacuo to give the titled compound (292 mg) as an oil.

Step 5. (S)—N-(4-fluorobicyclo[4.2.0]octa-1,3,5-trien-7-yl)-N'-hydroxy-4-(2-(sulfamoylamino)ethoxy)-1,2,5-oxadiazole-3-carboximidamide

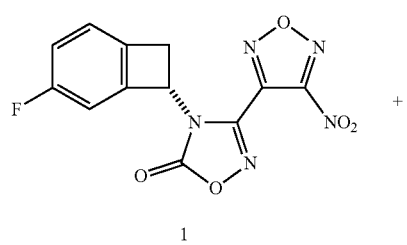

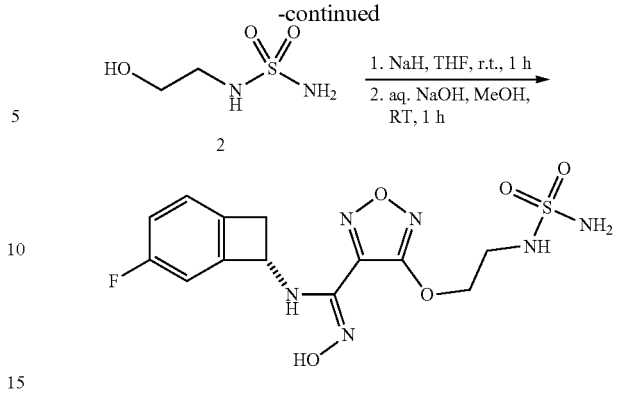

To a stirred solution of (S)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one (1.33 g, 4.16 mmol) and N-(2-hydroxyethyl)sulfamide (583 mg, 4.16 mmol) in THF (30 mL) was added NaH (499 mg, 60%, 12.48 mmol) in small portions at 15° C. After the addition was finished, the reaction was stirred at 15° C. for 1 h before aq. NaOH (3.0 mL, 3.0 mmol, 3M) was added slowly. The reaction mixture was stirred at 15° C. for another 1 h. Aqueous HCl solution (6.0 M) was then added to adjust the pH ~5. The mixture was concentrated in vacuo. The residue was purified by HPLC on a GILSON 281 instrument fitted with a Waters XSELECT C18 150*30 mm*5 um using water (0.1% FA)-CH₃CN to give the title compound (710 mg) as a solid. ¹H NMR (400 MHz, CD₃OD) δ 7.13 (dd, J=7.9, 4.0 Hz, 1H), 6.97-7.05 (m, 1H), 6.90 (br d, J=7.5 Hz, 1H), 5.08 (m, 1H), 4.55 (t, J=5.2 Hz, 2H), 3.49-3.55 (m, 3H), 3.05-3.08 (m, 1H); ESI MS m/z 387.1 [M+H+].

Example 2. (S)—N-(4-fluorobicyclo[4.2.0]octa-1(6),2,4-trien-7-yl)-N'-hydroxy-4-((1-(2-hydroxyacetyl)azetidin-3-yl)oxy)-1,2,5-oxadiazole-3-carboximidamide

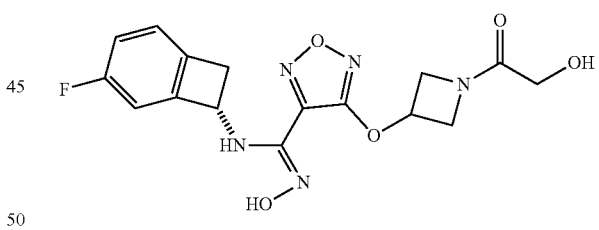

Step 1. (S)-tert-butyl 3-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)azetidine-1-carboxylate

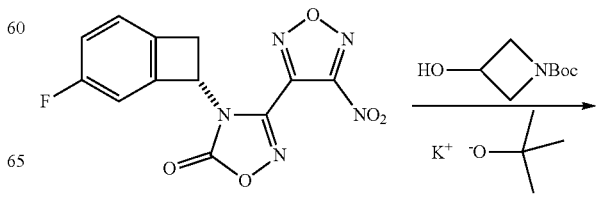

-continued

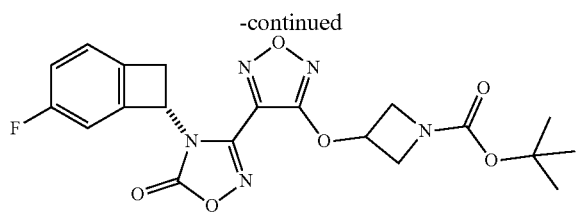

To a stirred solution of tert-butyl 3-hydroxyazetidine-1-carboxylate (163 mg, 0.940 mmol) in dry THF (6.3 mL) was added potassium tert-butoxide (1.0 M in THF, 689 μL, 0.689 mmol) at RT. The mixture was stirred at RT for about 2 min before (S)-(4-(4-fluorobicyclo[4.2.0]octa-1(6),2,4-trien-7-yl)-3-(4-nitro-1,2,5-oxadiazol-3-yl)-1,2,4-oxadiazol-5(4H)-one was added (200 mg, 0.627 mmol). The mixture was stirred at RT for 2 h, quenched with addition of HCl (1.0 M in water, 689 μl, 0.689 mmol), then partitioned between EtOAc (20 mL) and water (20 mL). The aqueous layer was extracted with EtOAc for three times. The combined organic phases were dried over Na$_2$SO$_4$, filtered, and concentrated in vacuo. The residue was purified by chromatography using Isco system (40 g gold silica gel RediSep column, 0-60% EtOAc/hexane as eluting solvent) to give the title compound as a solid (225 mg). LCMS m/z: 446.1 (M+H).

Step 2. (S)-3-(4-(azetidin-3-yloxy)-1,2,5-oxadiazol-3-yl)-4-(4-fluorobicyclo[4.2.0]octa-1(6),2,4-trien-7-yl)-1,2,4-oxadiazol-5(4H)-one, HCl

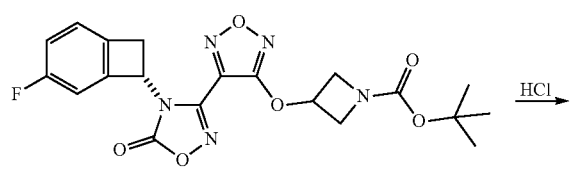

A mixture of (S)-tert-butyl 3-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)azetidine-1-carboxylate (220 mg, 0.494 mmol) in a HCl dioxane solution (4.0 M, 6.17 mL, 24.7 mmol) was stirred at RT for 1 h, and then concentrated in vacuo to give the desired product as a solid, which was used directly in the next step. LCMS m/z 346.1 (M+H).

Step 3. (S)-4-(4-fluorobicyclo[4.2.0]octa-1(6),2,4-trien-7-yl)-3-(4-((1-(2-hydroxyacetyl)azetidin-3-yl)oxy)-1,2,5-oxadiazol-3-yl)-1,2,4-oxadiazol-5(4H)-one

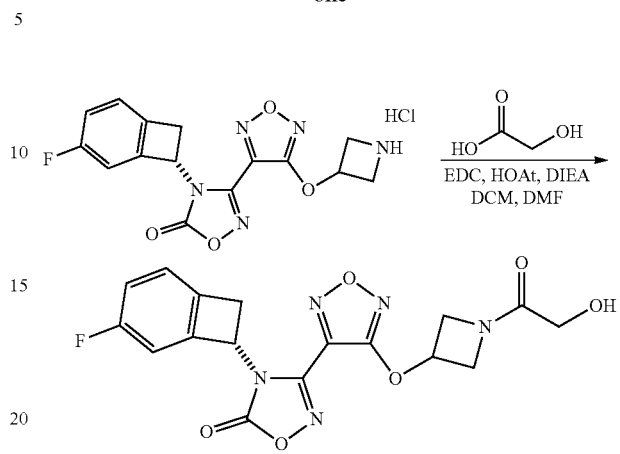

To a stirred solution of glycolic acid (19.92 mg, 0.262 mmol), 1-hydroxy-7-azabenzotriazole (HOAt) (23.18 mg, 0.170 mmol) and N-(3-dimethylaminopropyl)-N'-ethylcarbodiimide hydrochloride (EDC, 32.6 mg, 0.170 mmol) in CH$_2$Cl$_2$ (1.3 mL) and DMF (0.2 mL) were added (S)-3-(4-(azetidin-3-yloxy)-1,2,5-oxadiazol-3-yl)-4-(4-fluorobicyclo[4.2.0]octa-(6),2,4-trien-7-yl)-1,2,4-oxadiazol-5(4H)-one, HCl (50 mg, 0.131 mmol) and DIEA (68.6 μL, 0.393 mmol). The mixture was stirred at RT for 2 h, diluted with DCM (10 mL), washed with 1.0 N aqueous HCl (~5 mL) and then sat aqueous NaHCO$_3$ (~5 mL). The organic phase was dried over Na$_2$SO$_4$, filtered, and concentrated in vacuo to give the crude product as a yellow solid, which was used in the next step without further purification. LCMS m/z 404.1 (M+H).

Step 4. (S)—N-(4-fluorobicyclo[4.2.0]octa-1(6),2,4-trien-7-yl)-N'-hydroxy-4-((1-(2-hydroxyacetyl)azetidin-3-yl)oxy)-1,2,5-oxadiazole-3-carboximidamide

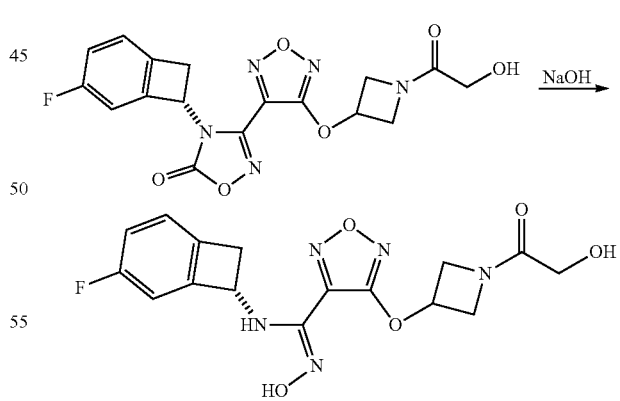

To a mixture of (S)-4-(4-fluorobicyclo[4.2.0]octa-1(6),2,4-trien-7-yl)-3-(4-((1-(2-hydroxyacetyl)azetidin-3-yl)oxy)-1,2,5-oxadiazol-3-yl)-1,2,4-oxadiazol-5(4H)-one (58.5 mg, 0.145 mmol) in THF (1.7 mL) and water (690 μL) was added NaOH (2 M in water, 218 μL, 0.435 mmol). The mixture was stirred at RT for 60 min, neutralized with addition of HCl (2.0 M in water, 218 μl, 0.435 mmol), and concentrated in vacuo. The residue was purified by mass-directed reversed-phase HPLC (19×100 mm, Waters CSH C18 column, 5p particle size, flow rate 25 mL/min, linear gradient, 8% ACN/H$_2$O to 50% ACN/H$_2$O, buffering with 0.16% formic acid) to give the title compound as a solid after lyophilization. LCMS m/z 378.3 (M+H) $^1$H NMR (500 MHz, CD$_3$OD): δ 7.11 (dd, J=5 Hz, J=8 Hz, 1H); 7.02-6.98 (m, 1H); 6.95-6.93 (m, 1H); 5.42-5.37 (m, 1H); 5.05 (br, s, 1H); 4.78-4.73 (m, 1H); 4.50-4.42 (m, 2H); 4.20-4.14 (m, 1H); 4.12 (br, s, 2H); 3.53 (d, J=15 Hz, 1H); 3.09 (d, J=15 Hz, 1H)

Example 3. (S)—N-(2-((4-(N-(4-fluorobicyclo[4.2.0]octa-1(6),2,4-trien-7-yl)-N'-hydroxycarbamimidoyl)-1,2,5-oxadiazol-3-yl)oxy)ethyl)acetamide

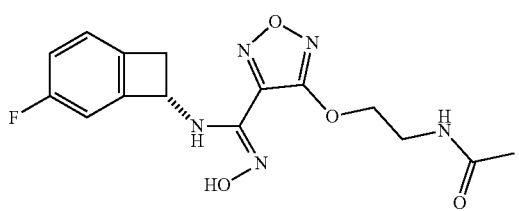 [SMILES: CC(=O)NCCOc1nonc1/C(=N/O)N[C@H]1Cc2ccc(F)cc21]

Step 1. (S)—N-(2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)ethyl)acetamide

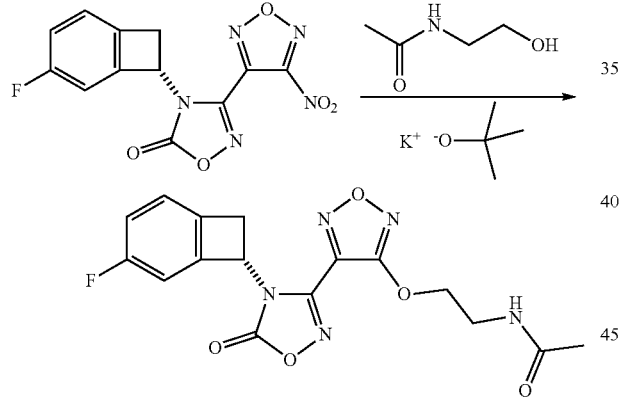

Following a similar procedure as described in Step 1 of Example 2, the title compound was obtained as a solid. LCMS m/z 376.1 (M+H)$^+$.

Step 2. (S)—N-(2-((4-(N-(4-fluorobicyclo[4.2.0]octa-1(6),2,4-trien-7-yl)-N'-hydroxycarbamimidoyl)-1,2,5-oxadiazol-3-yl)oxy)ethyl)acetamide

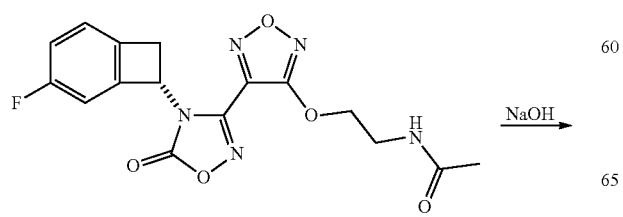

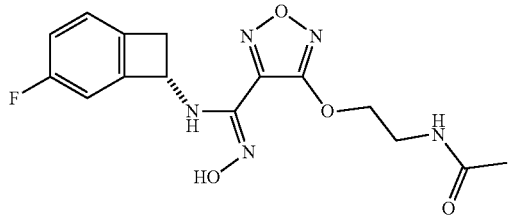

Following a similar procedure as described in Step 4 of Example 2, the titled compound was obtained as a solid. LCMS m/z 350.3 (M+H)$^+$; $^1$H NMR (500 MHz, CD$_3$OD): δ 7.13-7.09 (m, 1H); 7.03-6.99 (m, 1H); 6.94-6.91 (m, 1H); 5.00 (s, br, 1H); 4.48 (t, J=5.0 Hz, 2H); 3.65 (t, J=5 Hz, 2H); 3.52 (d, J=10.0 Hz, 1H); 3.09 (d, J=10 Hz, 1H); 1.94 (s, 3H)

Example 4. (S)-2-((4-(N-(4-fluorobicyclo[4.2.0]octa-1(6),2,4-trien-7-yl)-N'-hydroxycarbamimidoyl)-1,2,5-oxadiazol-3-yl)oxy)-N-(2-hydroxyethyl)acetamide

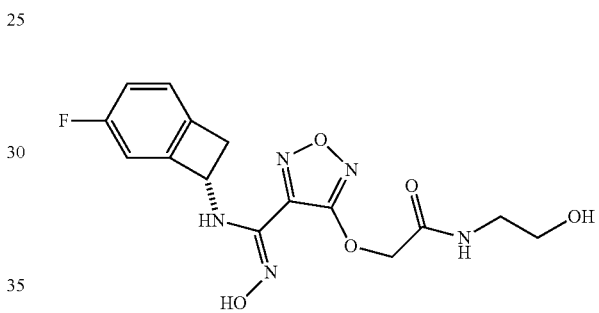

Step 1. tert-butyl (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)acetate

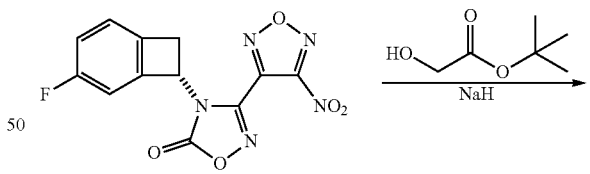

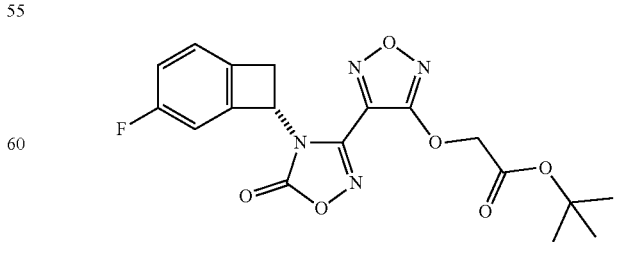

To a stirred solution of tert-butyl 2-hydroxyacetate (267 mg, 2.02 mmol) in dry THF (16.8 mL) was added sodium hydride (60% in oil) (62.0 mg, 1.55 mmol) at RT. The mixture was stirred at RT for about 2 min before (S)-4-(4-fluorobicyclo[4.2.0]octa-1(6),2,4-trien-7-yl)-3-(4-nitro-1,2,5-oxadiazol-3-yl)-1,2,4-oxadiazol-5(4H)-one (430 mg, 1.347 mmol) was added. The mixture was stirred at RT for 1 h, quenched by cold water (20 mL), extracted with EtOAc (50 mL×3). The organic phases were combined, dried over $Na_2SO_4$, filtered, and concentrated in vacuo. The residue was purified by chromatography (Isco system, 80 g silica gel gold column, 0-60% EtOAc/Hexane as eluting solvent) to give the title compound as an oil. LCMS m/z 405.0 (M+H)$^+$.

Step 2. (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)acetic acid

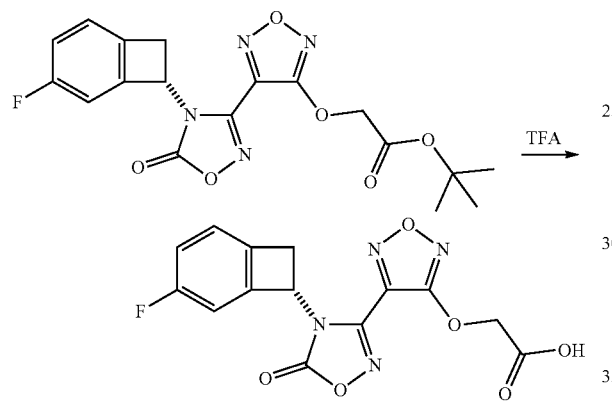

A mixture of tert-butyl (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)acetate (540 mg, 1.335 mmol) in $CH_2Cl_2$ (8.3 mL) and TFA (8.2 mL) was stirred at RT for 2 h, then concentrated in vacuo to give the title compound as a solid. LCMS m/z 349.1 (M+H)$^+$.

Step 3. (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)-N-(2-hydroxyethyl)acetamide

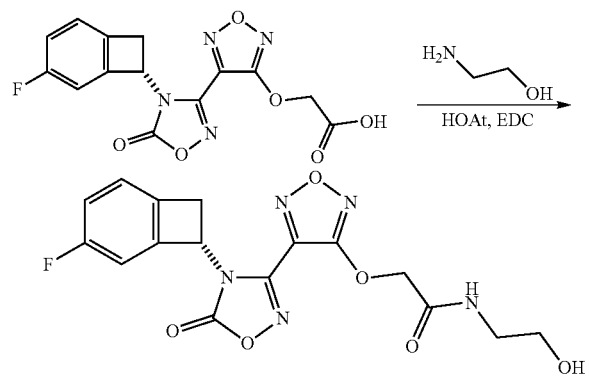

To a stirred solution of (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)acetic acid (45 mg, 0.129 mmol), 1-hydroxy-7-azabenzotriazole (22.86 mg, 0.168 mmol) and EDC (32.2 mg, 0.168 mmol) in $CH_2Cl_2$ (1.0 mL) was added a solution of ethanolamine (15.6 µL, 0.25 mmol) in DMF (500 µL). The mixture was stirred at RT for 2 h, diluted with DCM (10 mL), washed with water (5 mL) and sat aqueous $NaHCO_3$ (5 mL). The organic phase was separated, dried over $Na_2SO_4$, filtered, and concentrated in vacuo to give the crude product as a solid, which was used in the next step without further purification. LCMS m/z 392.1 (M+H)$^+$.

Step 4. (S)-2-((4-(N-(4-fluorobicyclo[4.2.0]octa-1(6),2,4-trien-7-yl)-N'-hydroxycarbamimidoyl)-1,2,5-oxadiazol-3-yl)oxy)-N-(2-hydroxyethyl)acetamide

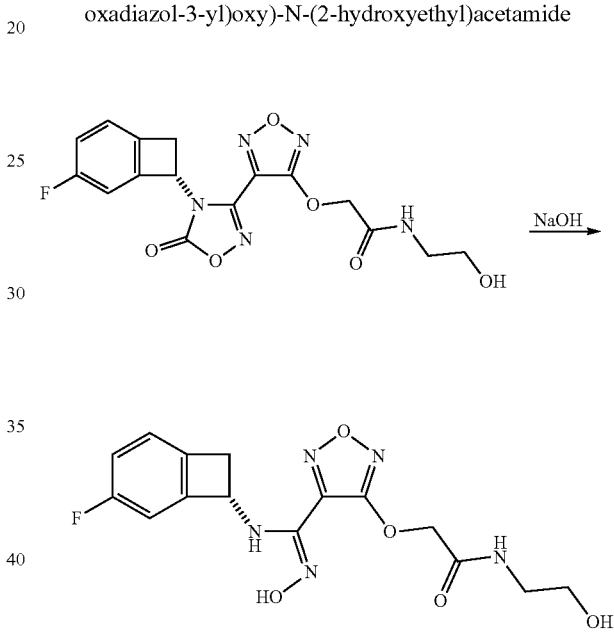

To a solution of (S)-2-((4-(4-(4-fluorobicyclo[4.2.0]octa-1(6),2,4-trien-7-yl)-5-oxo-4,5-dihydro-1,2,4-oxadiazol-3-yl)-1,2,5-oxadiazol-3-yl)oxy)-N-(2-hydroxyethyl)acetamide (50.5 mg) in THF (1 mL), water (0.5 mL), and methanol (0.5 mL) was added NaOH (2 M in water, 0.323 mL, 0.645 mmol). The mixture was stirred at RT for 0.5 h, quenched with addition of TFA (0.080 mL, 1.032 mmol), then concentrated in vacuo. The residue was purified by mass-directed reversed-phase HPLC (19×100 mm, Waters CSH C18 column, 19×100 mm, 5p particle size, flow rate 25 mL/min, linear gradient, 20% ACN/$H_2O$ to 55% ACN/$H_2O$, total run time 8 min, buffering with 0.16% TFA) to give the titled compound as a solid. LCMS m/z (M+H) calc'd: 366.1; found (M+H): 366.4. $^1$H NMR (500 MHz, $CD_3OD$): δ7.13-7.10 (m, 1H); 7.03-6.93 (m, 2H); 5.20 (br, s, 1H); 4.94 (br, s, 2H); 3.66 (m, 2H); 3.57 (d, J=10 Hz, 1H); 3.40 (m, 2H); 3.10 (d, J=10 Hz, 1H).

Using the general methodology disclosed in Scheme 1, Examples 1-4, and general knowledge in organic synthesis, compounds in Table 1 were prepared.

TABLE 1

| Ex. # | Structure | Name | Mass [M + H]+ |
|---|---|---|---|
| 5 | 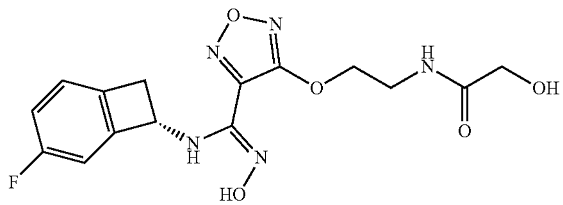 [SMILES: O=C(CO)NCCOc1nonc1/C(=N/O)N[C@H]1Cc2ccc(F)cc21] | N-{2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]ethyl}-2-hydroxyacetamide | 366.1 |
| 6 | 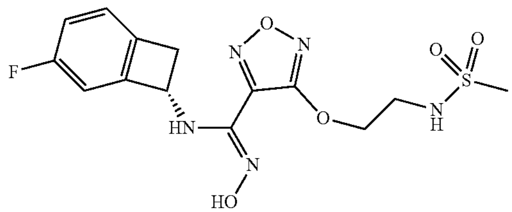 [SMILES: CS(=O)(=O)NCCOc1nonc1/C(=N/O)N[C@H]1Cc2ccc(F)cc21] | N-[(7S)-4-fluorobicyclo[4.2.0]octa-1,3,5-trien-7-yl]-N'-hydroxy-4-{2-[(methylsulfonyl)amino]ethoxy}-1,2,5-oxadiazole-3-carboximidamide | 386.1 |
| 7 | 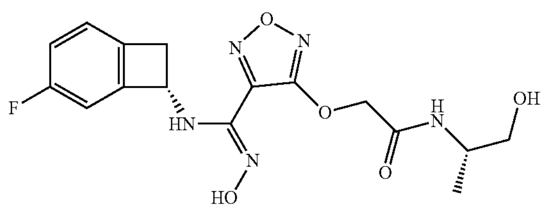 [SMILES: C[C@@H](CO)NC(=O)COc1nonc1/C(=N/O)N[C@H]1Cc2ccc(F)cc21] | 2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-N-[(2S)-1-hydroxypropan-2-yl]acetamide | 380.1 |
| 8 | 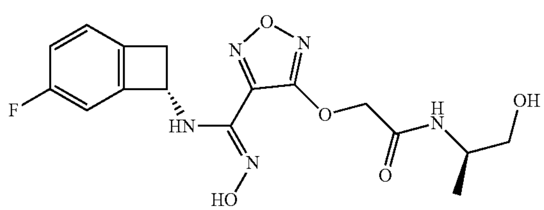 [SMILES: C[C@H](CO)NC(=O)COc1nonc1/C(=N/O)N[C@H]1Cc2ccc(F)cc21] | 2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-N-[(2R)-1-hydroxypropan-2-yl]acetamide | 380.1 |
| 9 | 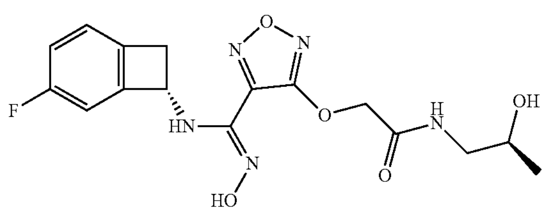 [SMILES: C[C@H](O)CNC(=O)COc1nonc1/C(=N/O)N[C@H]1Cc2ccc(F)cc21] | 2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-N-[(2S)-2-hydroxypropyl]acetamide | 380.1 |
| 10 | 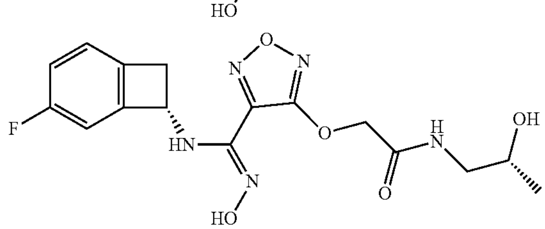 | 2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-N-[(2R)-2-hydroxypropyl]acetamide | 380.1 |
| 11 | 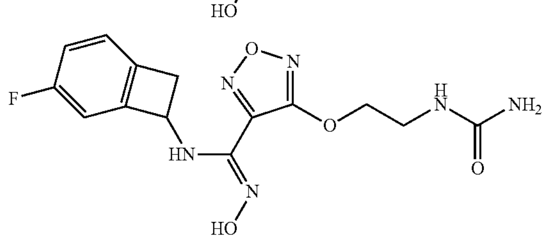 | 4-[2-(carbamoylamino)ethoxy]-N-(4-fluorobicyclo[4.2.0]octa-1,3,5-trien-7-yl)-N'-hydroxy-1,2,5-oxadiazole-3-carboximidamide | 351.1 |

TABLE 1-continued

| Ex. # | Structure | Name | Mass [M + H]+ |
|---|---|---|---|
| 12 | 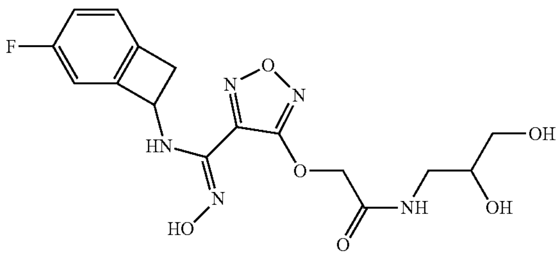 [SMILES: O=C(COc1nonc1/C(=N/O)NC1Cc2ccc(F)cc21)NCC(O)CO] | N-(2,3-dihydroxypropyl)-2-({4-[N-(4-fluorobicyclo[4.2.0]octa-1,3,5-trien-7-yl)-N'-hydroxycarbamimidoyl]-1,2,5-oxadiazol-3-yl}oxy)acetamide | 396.1 |
| 13 | 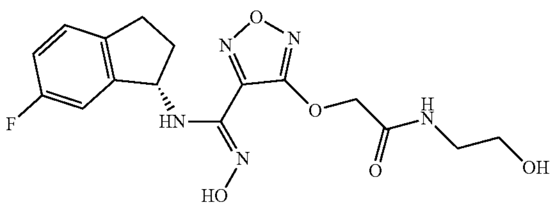 [SMILES: O=C(COc1nonc1/C(=N/O)N[C@H]1CCc2ccc(F)cc21)NCCO] | 2-[(4-{N-[(1S)-6-fluoro-2,3-dihydro-1H-inden-1-yl]-N'-hydroxycarbamimidoyl}-1,2,5-oxadiazol-3-yl)oxy]-N-(2-hydroxyethyl)acetamide | 380.1 |
| 14 | 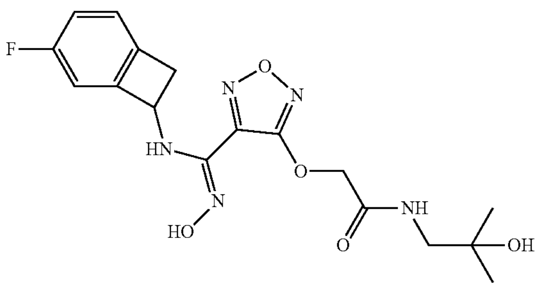 [SMILES: CC(C)(O)CNC(=O)COc1nonc1/C(=N/O)NC1Cc2ccc(F)cc21] | 2-({4-[N-(4-fluorobicyclo[4.2.0]octa-1,3,5-trien-7-yl)-N'-hydroxycarbamimidoyl]-1,2,5-oxadiazol-3-yl}oxy)-N-(2-hydroxy-2-methylpropyl)acetamide | 394.2 |
| 15 | 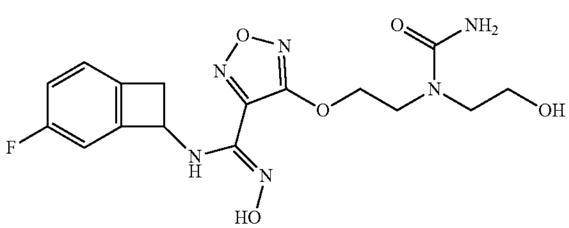 [SMILES: NC(=O)N(CCO)CCOc1nonc1/C(=N/O)NC1Cc2ccc(F)cc21] | 4-{2-[carbamoyl(2-hydroxyethyl)amino]ethoxy}-N-(4-fluorobicyclo[4.2.0]octa-1,3,5-trien-7-yl)-N'-hydroxy-1,2,5-oxadiazole-3-carboximidamide | 395.1 |
| 16 | 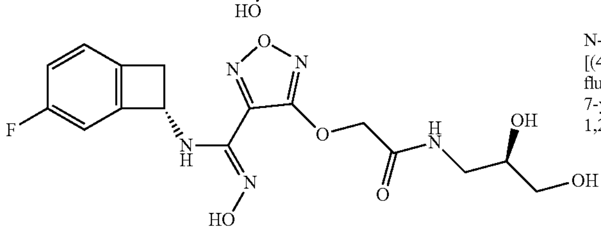 | N-[(2R)-2,3-dihydroxypropyl]-2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]acetamide | 396.1 |
| 17 | 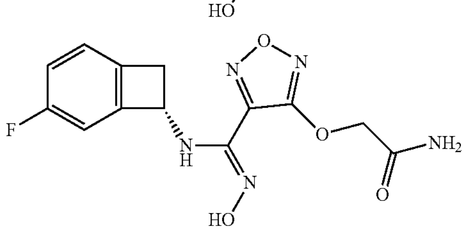 | 2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]acetamide | 322.1 |
| 18 | 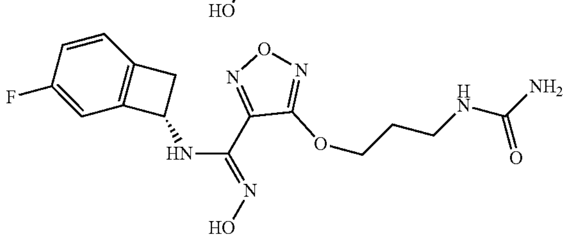 | 4-[3-(carbamoylamino)propoxy]-N-[(7S)-4-fluorobicyclo[4.2.0]octa-1,3,5-trien-7-yl]-N'-hydroxy-1,2,5-oxadiazole-3-carboximidamide | 365.1 |

TABLE 1-continued

| Ex. # | Structure | Name | Mass [M + H]+ |
|---|---|---|---|
| 19 | 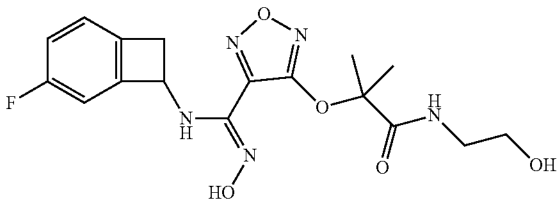 [SMILES: CC(C)(Oc1nonc1/C(=N/O)NC1Cc2ccc(F)cc21)C(=O)NCCO] | 2-({4-[N-(4-fluorobicyclo[4.2.0]octa-1,3,5-trien-7-yl)-N'-hydroxycarbamimidoyl]-1,2,5-oxadiazol-3-yl}oxy)-N-(2-hydroxyethyl)-2-methylpropanamide | 394.2 |
| 20 | 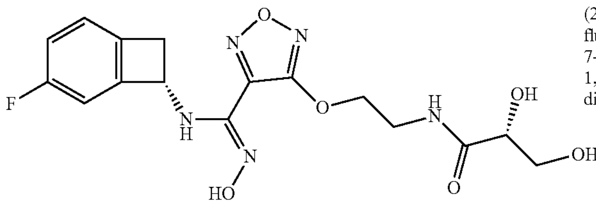 [SMILES: O=C(NCCOc1nonc1/C(=N/O)N[C@H]1Cc2ccc(F)cc21)[C@H](O)CO] | (2R)-N-{2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]ethyl}-2,3-dihydroxypropanamide | 396.1 |
| 21 | 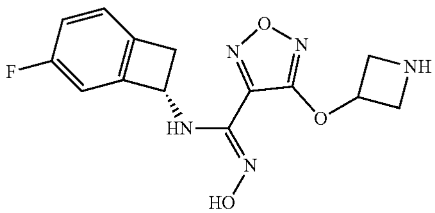 [SMILES: O/N=C(\N[C@H]1Cc2ccc(F)cc21)c1nonc1OC1CNC1] | 4-[(azetidin-3-yl)oxy]-N-[(7S)-4-fluorobicyclo[4.2.0]octa-1,3,5-trien-7-yl]-N'-hydroxy-1,2,5-oxadiazole-3-carboximidamide | 320.1 |
| 22 | 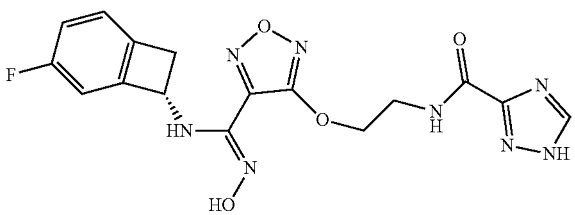 [SMILES: O=C(NCCOc1nonc1/C(=N/O)N[C@H]1Cc2ccc(F)cc21)c1nc[nH]n1] | N-{2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]ethyl}-1H-1,2,4-triazole-3-carboxamide | 403.1 |
| 23 | 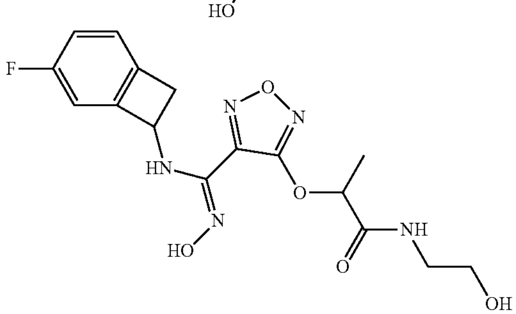 | 2-({4-[N-(4-fluorobicyclo[4.2.0]octa-1,3,5-trien-7-yl)-N'-hydroxycarbamimidoyl]-1,2,5-oxadiazol-3-yl}oxy)-N-(2-hydroxyethyl)propanamide | 380.1 |
| 24 | 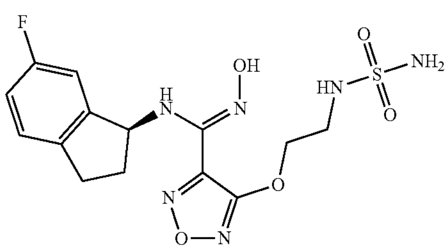 [SMILES: NS(=O)(=O)NCCOc1nonc1/C(=N/O)N[C@H]1CCc2ccc(F)cc21] | N-[(1S)-6-fluoro-2,3-dihydro-1H-inden-1-yl]-N'-hydroxy-4-[2-(sulfamoylamino)ethoxy]-1,2,5-oxadiazole-3-carboximidamide | 401.1 |
| 25 | 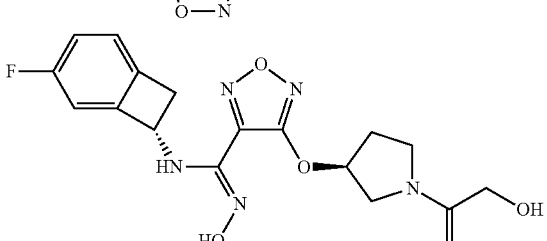 | N-[(7S)-4-fluorobicyclo[4.2.0]octa-1,3,5-trien-7-yl]-N'-hydroxy-4-{[(3S)-1-(hydroxyacetyl)pyrrolidin-3-yl]oxy}-1,2,5-oxadiazole-3-carboximidamide | 392.1 |

TABLE 1-continued

| Ex. # | Structure | Name | Mass [M + H]+ |
|---|---|---|---|
| 26 | 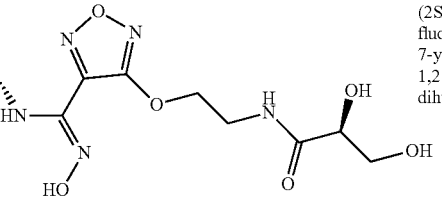 | (2S)-N-{2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]ethyl}-2,3-dihydroxypropanamide | 396.1 |
| 27 | 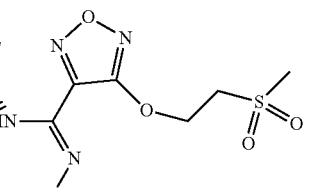 | N-[(7S)-4-fluorobicyclo[4.2.0]octa-1,3,5-trien-7-yl]-N'-hydroxy-4-[2-(methylsulfonyl)ethoxy]-1,2,5-oxadiazole-3-carboximidamide | 371.1 |
| 28 | 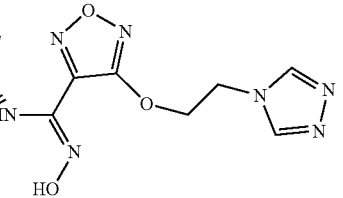 | N-[(7S)-4-fluorobicyclo[4.2.0]octa-1,3,5-trien-7-yl]-N'-hydroxy-4-[2-(4H-1,2,4-triazol-4-yl)ethoxy]-1,2,5-oxadiazole-3-carboximidamide | 360.1 |
| 29 | 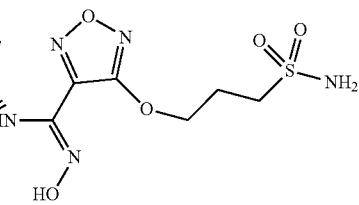 | N-[(7S)-4-fluorobicyclo[4.2.0]octa-1,3,5-trien-7-yl]-N'-hydroxy-4-(3-sulfamoylpropoxy)-1,2,5-oxadiazole-3-carboximidamide | 386.1 |
| 30 | 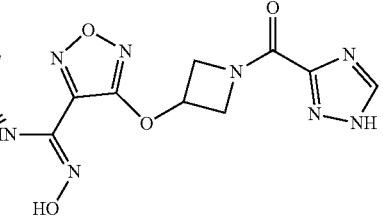 | N-[(7S)-4-fluorobicyclo[4.2.0]octa-1,3,5-trien-7-yl]-N'-hydroxy-4-{[1-(1H-1,2,4-triazole-3-carbonyl)azetidin-3-yl]oxy}-1,2,5-oxadiazole-3-carboximidamide | 415.1 |
| 31 | 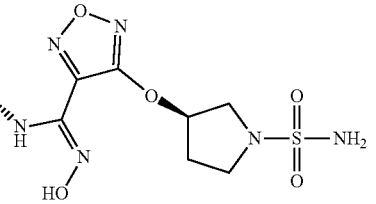 | N-[(7S)-4-fluorobicyclo[4.2.0]octa-1,3,5-trien-7-yl]-N'-hydroxy-4-{[(3R)-1-sulfamoylpyrrolidin-3-yl]oxy}-1,2,5-oxadiazole-3-carboximidamide | 413.1 |
| 32 | 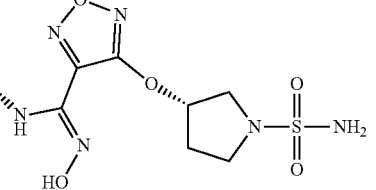 | N-[(7S)-4-fluorobicyclo[4.2.0]octa-1,3,5-trien-7-yl]-N'-hydroxy-4-{[(3S)-1-sulfamoylpyrrolidin-3-yl]oxy}-1,2,5-oxadiazole-3-carboximidamide | 413.1 |

TABLE 1-continued

| Ex. # | Structure | Name | Mass [M + H]+ |
|---|---|---|---|
| 33 | 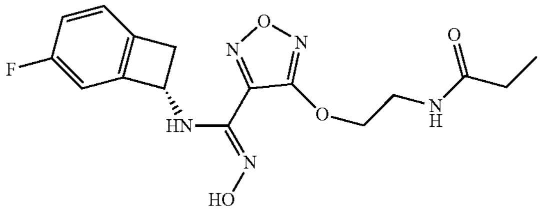 [SMILES: CCC(=O)NCCOc1nonc1/C(=N/O)N[C@H]1Cc2ccc(F)cc21] | N-{2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]ethyl}propanamide | 364.1 |
| 34 | 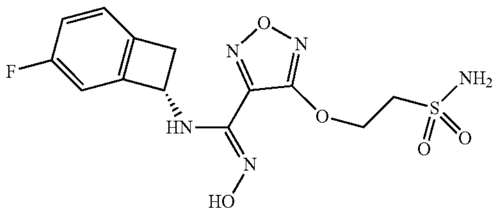 [SMILES: NS(=O)(=O)CCOc1nonc1/C(=N/O)N[C@H]1Cc2ccc(F)cc21] | N-[(7S)-4-fluorobicyclo[4.2.0]octa-1,3,5-trien-7-yl]-N'-hydroxy-4-(2-sulfamoylethoxy)-1,2,5-oxadiazole-3-carboximidamide | 372.1 |
| 35 | 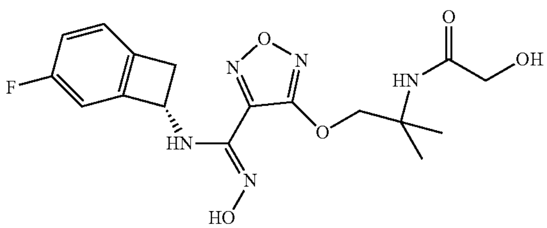 [SMILES: CC(C)(COc1nonc1/C(=N/O)N[C@H]1Cc2ccc(F)cc21)NC(=O)CO] | N-{1-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-2-methylpropan-2-yl}-2-hydroxyacetamide | 394.2 |
| 36 | 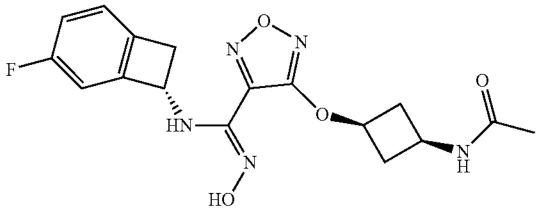 [SMILES: CC(=O)N[C@H]1C[C@@H](Oc2nonc2/C(=N/O)N[C@H]2Cc3ccc(F)cc32)C1] | N-{cis-3-[(4-{N-[(7S)-4-fluorobicyclo[4.2.0]octa-1,3,5-trien-7-yl]-N'-hydroxycarbamimidoyl}-1,2,5-oxadiazol-3-yl)oxy]cyclobutyl}acetamide | 376.1 |
| 37 | 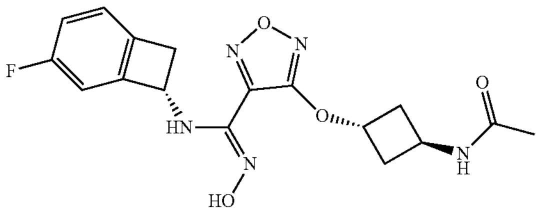 [SMILES: CC(=O)N[C@H]1C[C@H](Oc2nonc2/C(=N/O)N[C@H]2Cc3ccc(F)cc32)C1] | N-{trans-3-[(4-{N-[(7S)-4-fluorobicyclo[4.2.0]octa-1,3,5-trien-7-yl]-N'-hydroxycarbamimidoyl}-1,2,5-oxadiazol-3-yl)oxy]cyclobutyl}acetamide | 376.1 |
| 38 | 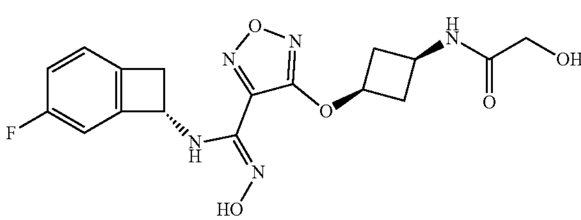 [SMILES: O=C(CO)N[C@H]1C[C@@H](Oc2nonc2/C(=N/O)N[C@H]2Cc3ccc(F)cc32)C1] | N-{cis-3-[(4-{N-[(7S)-4-fluorobicyclo[4.2.0]octa-1,3,5-trien-7-yl]-N'-hydroxycarbamimidoyl}-1,2,5-oxadiazol-3-yl)oxy]cyclobutyl}-2-hydroxyacetamide | 392.1 |
| 39 | 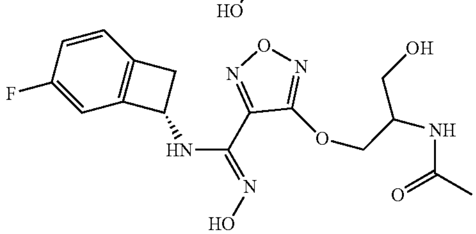 | N-{1-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-3-hydroxypropan-2-yl}acetamide | 380.1 |

TABLE 1-continued

| Ex. # | Structure | Name | Mass [M + H]+ |
|---|---|---|---|
| 40 | 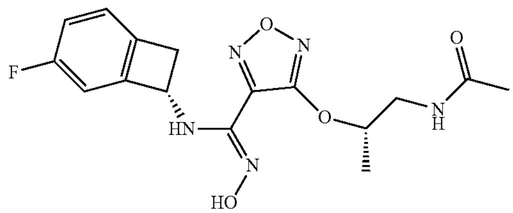 [SMILES: CC(=O)NC[C@H](C)Oc1nonc1/C(=N/O)N[C@H]1Cc2ccc(F)cc21] | N-{(2S)-2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]propyl}acetamide | 364.1 |
| 41 | 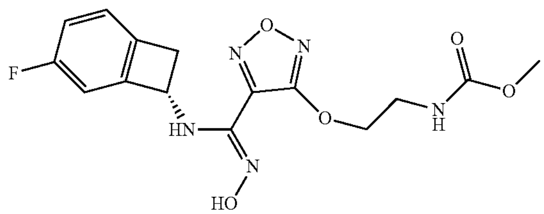 [SMILES: COC(=O)NCCOc1nonc1/C(=N/O)N[C@H]1Cc2ccc(F)cc21] | methyl {2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]ethyl}carbamate | 366.1 |
| 42 | 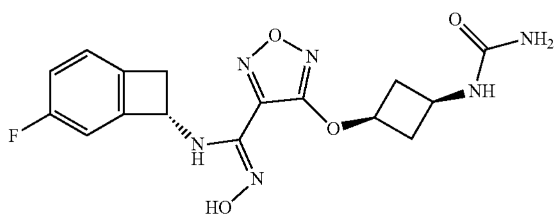 [SMILES: NC(=O)N[C@H]1C[C@@H](Oc2nonc2/C(=N/O)N[C@H]2Cc3ccc(F)cc32)C1] | 4-{[cis-3-(carbamoylamino)cyclobutyl]oxy}-N-[(7S)-4-fluorobicyclo[4.2.0]octa-1,3,5-trien-7-yl]-N'-hydroxy-1,2,5-oxadiazole-3-carboximidamide | 377.1 |
| 43 | 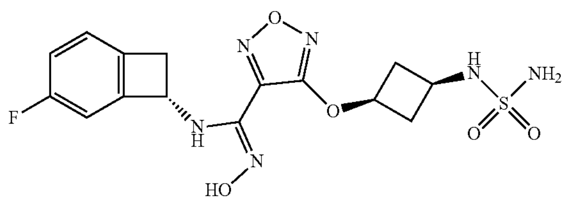 [SMILES: NS(=O)(=O)N[C@H]1C[C@@H](Oc2nonc2/C(=N/O)N[C@H]2Cc3ccc(F)cc32)C1] | N-[(7S)-4-fluorobicyclo[4.2.0]octa-1,3,5-trien-7-yl]-N'-hydroxy-4-{[cis-3-(sulfamoylamino)cyclobutyl]oxy}-1,2,5-oxadiazole-3-carboximidamide | 413.1 |
| 44 | 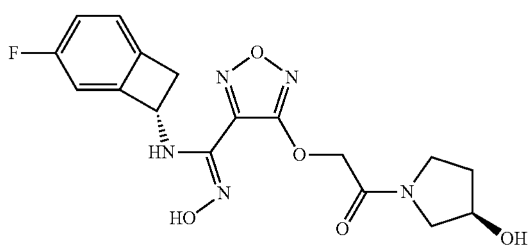 [SMILES: O=C(COc1nonc1/C(=N/O)N[C@H]1Cc2ccc(F)cc21)N1CC[C@@H](O)C1] | N-[(7S)-4-fluorobicyclo[4.2.0]octa-1,3,5-trien-7-yl]-N'-hydroxy-4-{2-[(3R)-3-hydroxypyrrolidin-1-yl]-2-oxoethoxy}-1,2,5-oxadiazole-3-carboximidamide | 392.1 |
| 45 | 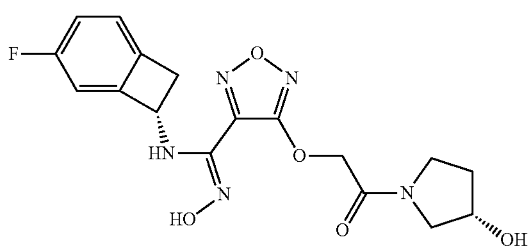 [SMILES: O=C(COc1nonc1/C(=N/O)N[C@H]1Cc2ccc(F)cc21)N1CC[C@H](O)C1] | N-[(7S)-4-fluorobicyclo[4.2.0]octa-1,3,5-trien-7-yl]-N'-hydroxy-4-{2-[(3S)-3-hydroxypyrrolidin-1-yl]-2-oxoethoxy}-1,2,5-oxadiazole-3-carboximidamide | 392.1 |
| 46 | 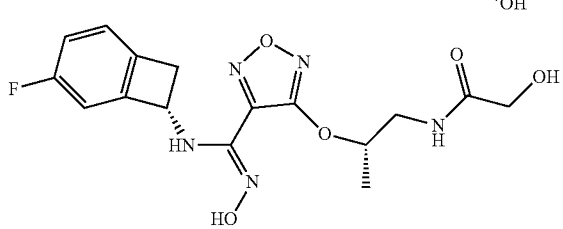 | N-{(2S)-2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]propyl}-2-hydroxyacetamide | 380.1 |

TABLE 1-continued

| Ex. # | Structure | Name | Mass [M + H]+ |
|---|---|---|---|
| 47 | 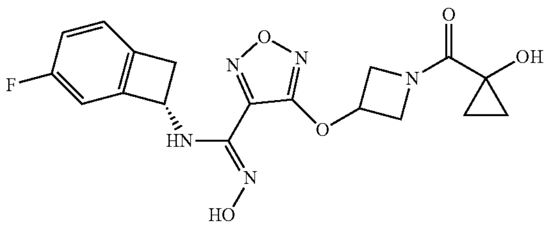 [SMILES: O=C(N1CC(Oc2nonc2/C(=N/O)N[C@H]2Cc3ccc(F)cc32)C1)C1(O)CC1] | N-[(7S)-4-fluorobicyclo[4.2.0]octa-1,3,5-trien-7-yl]-N'-hydroxy-4-{[1-(1-hydroxycyclopropane-1-carbonyl)azetidin-3-yl]oxy}-1,2,5-oxadiazole-3-carboximidamide | 404.1 |
| 48 | 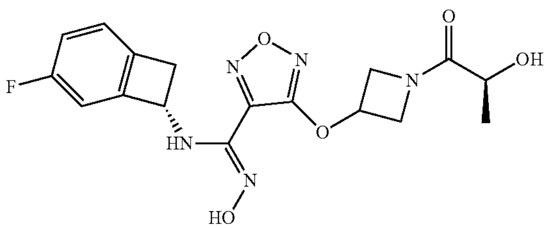 [SMILES: C[C@H](O)C(=O)N1CC(Oc2nonc2/C(=N/O)N[C@H]2Cc3ccc(F)cc32)C1] | N-[(7S)-4-fluorobicyclo[4.2.0]octa-1,3,5-trien-7-yl]-N'-hydroxy-4-({1-[(2S)-2-hydroxypropanoyl]azetidin-3-yl}oxy)-1,2,5-oxadiazole-3-carboximidamide | 392.1 |
| 49 | 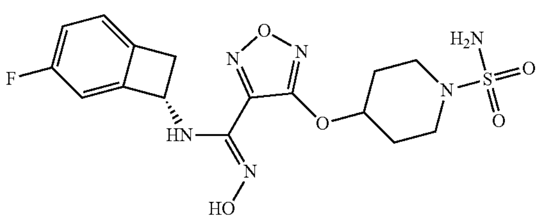 [SMILES: NS(=O)(=O)N1CCC(Oc2nonc2/C(=N/O)N[C@H]2Cc3ccc(F)cc32)CC1] | N-[(7S)-4-fluorobicyclo[4.2.0]octa-1,3,5-trien-7-yl]-N'-hydroxy-4-[(1-sulfamoylpiperidin-4-yl)oxy]-1,2,5-oxadiazole-3-carboximidamide | 427.1 |
| 50 | 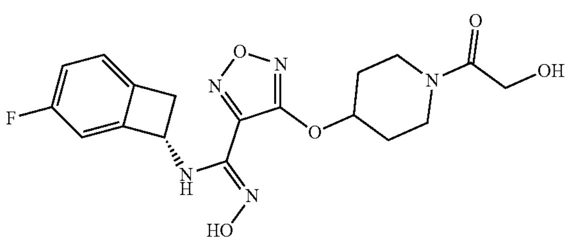 [SMILES: O=C(CO)N1CCC(Oc2nonc2/C(=N/O)N[C@H]2Cc3ccc(F)cc32)CC1] | N-[(7S)-4-fluorobicyclo[4.2.0]octa-1,3,5-trien-7-yl]-N'-hydroxy-4-{[1-(hydroxyacetyl)piperidin-4-yl]oxy}-1,2,5-oxadiazole-3-carboximidamide | 406.2 |
| 51 | 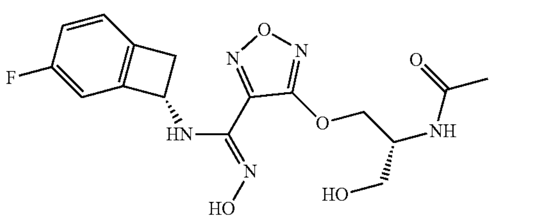 [SMILES: CC(=O)N[C@H](CO)COc1nonc1/C(=N/O)N[C@H]1Cc2ccc(F)cc21] | N-{(2R)-1-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-3-hydroxypropan-2-yl}acetamide | 380.1 |
| 52 | 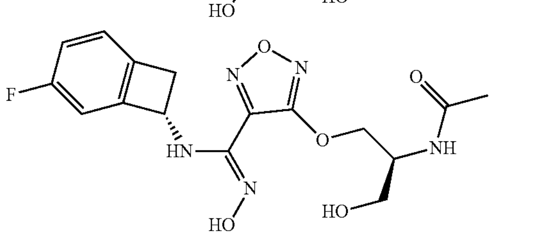 | N-{(2S)-1-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-3-hydroxypropan-2-yl}acetamide | 380.1 |
| 53 | 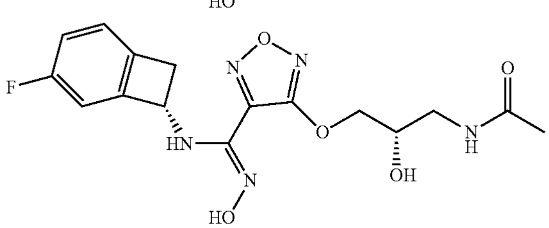 | N-{(2S)-3-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-2-hydroxypropyl}acetamide | 380.1 |

TABLE 1-continued

| Ex. # | Name | Mass [M + H]+ |
|---|---|---|
| 54 | N-[(7S)-4-fluorobicyclo[4.2.0]octa-1,3,5-trien-7-yl]-N'-hydroxy-4-{[(2S)-1-(hydroxyacetyl)azetidin-2-yl]methoxy}-1,2,5-oxadiazole-3-carboximidamide | 392.1 |
| 55 | N-{(2S)-2-[(4-{N-[(7S)-4-fluorobicyclo[4.2.0]octa-1,3,5-trien-7-yl]-N'-hydroxycarbamimidoyl}-1,2,5-oxadiazol-3-yl)oxy]-3-hydroxypropyl}acetamide | 380.1 |
| 56 | N-{trans-3-[(4-{N-[(7S)-4-fluorobicyclo[4.2.0]octa-1,3,5-trien-7-yl]-N'-hydroxycarbamimidoyl}-1,2,5-oxadiazol-3-yl)oxy]cyclobutyl}-2-hydroxyacetamide | 392.1 |
| 57 | 4-{[trans-3-(carbamoylamino)cyclobutyl]oxy}-N-[(7S)-4-fluorobicyclo[4.2.0]octa-1,3,5-trien-7-yl]-N'-hydroxy-1,2,5-oxadiazole-3-carboximidamide | 377.1 |
| 58 | N-[(7S)-4-fluorobicyclo[4.2.0]octa-1,3,5-trien-7-yl]-N'-hydroxy-4-{[(2R)-1-(hydroxyacetyl)pyrrolidin-2-yl]methoxy}-1,2,5-oxadiazole-3-carboximidamide | 406.2 |
| 59 | N-[(7S)-4-fluorobicyclo[4.2.0]octa-1,3,5-trien-7-yl]-N'-hydroxy-4-{[1-(hydroxyacetyl)azetidin-3-yl]methoxy}-1,2,5-oxadiazole-3-carboximidamide | 392.1 |
| 60 | N-[(7S)-4-fluorobicyclo[4.2.0]octa-1,3,5-trien-7-yl]-N'-hydroxy-4-{[(3R)-1-(hydroxyacetyl)pyrrolidin-3-yl]oxy}-1,2,5-oxadiazole-3-carboximidamide | 392.1 |

TABLE 1-continued

| Ex. # | Structure | Name | Mass [M + H]+ |
|---|---|---|---|
| 61 | 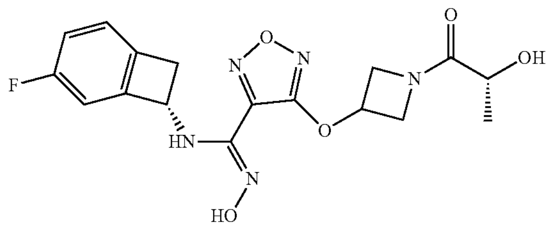 [SMILES: C[C@@H](O)C(=O)N1CC(Oc2nonc2/C(=N/O)N[C@H]2Cc3ccc(F)cc32)C1] | N-((S)-4-fluorobicyclo[4.2.0]octa-1(6),2,4-trien-7-yl)-N'-hydroxy-4-((1-((R)-2-hydroxypropanoyl)azetidin-3-yl)oxy)-1,2,5-oxadiazole-3-carboximidamide | 392.3 |
| 62 | 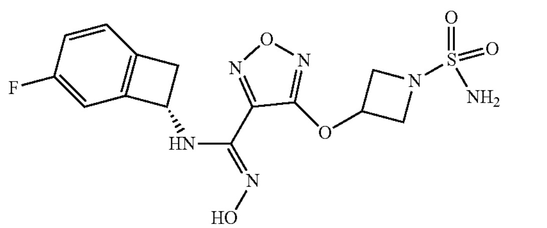 [SMILES: NS(=O)(=O)N1CC(Oc2nonc2/C(=N/O)N[C@H]2Cc3ccc(F)cc32)C1] | (S,Z)-N-(4-fluorobicyclo[4.2.0]octa-1(6),2,4-trien-7-yl)-N'-hydroxy-4-((1-sulfamoylazetidin-3-yl)oxy)-1,2,5-oxadiazole-3-carboximidamide | 399.0 |
| 63 | 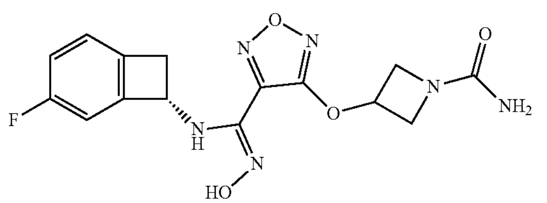 [SMILES: NC(=O)N1CC(Oc2nonc2/C(=N/O)N[C@H]2Cc3ccc(F)cc32)C1] | (S,Z)-3-((4-(N-(4-fluorobicyclo[4.2.0]octa-1(6),2,4-trien-7-yl)-N'-hydroxycarbamimidoyl)-1,2,5-oxadiazol-3-yl)oxy)azetidine-1-carboxamide | 363.2 |
| 64 | 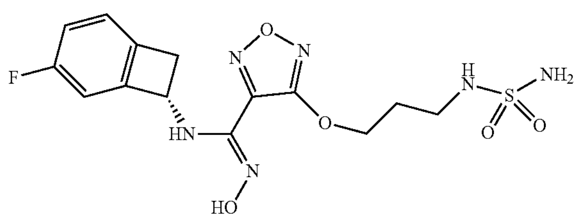 [SMILES: NS(=O)(=O)NCCCOc1nonc1/C(=N/O)N[C@H]1Cc2ccc(F)cc21] | (S,Z)-N-(4-fluorobicyclo[4.2.0]octa-1(6),2,4-trien-7-yl)-N'-hydroxy-4-(3-(sulfamoylamino)propoxy)-1,2,5-oxadiazole-3-carboximidamide | 401.2 |
| 65 | 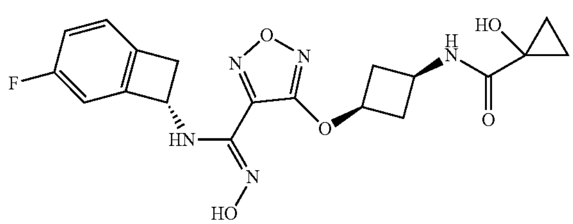 [SMILES: O=C(N[C@H]1C[C@@H](Oc2nonc2/C(=N/O)N[C@H]2Cc3ccc(F)cc32)C1)C1(O)CC1] | N-((1R,3s)-3-((4-((Z)-N-((S)-4-fluorobicyclo[4.2.0]octa-1(6),2,4-trien-7-yl)-N'-hydroxycarbamimidoyl)-1,2,5-oxadiazol-3-yl)oxy)cyclobutyl)-1-hydroxycyclopropanecarboxamide | 418.3 |
| 66 | 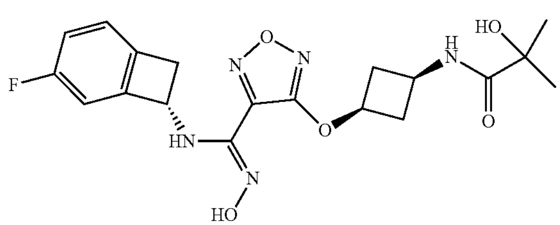 [SMILES: CC(C)(O)C(=O)N[C@H]1C[C@@H](Oc2nonc2/C(=N/O)N[C@H]2Cc3ccc(F)cc32)C1] | N-((1R,3s)-3-((4-((Z)-N-((S)-4-fluorobicyclo[4.2.0]octa-1(6),2,4-trien-7-yl)-N'-hydroxycarbamimidoyl)-1,2,5-oxadiazol-3-yl)oxy)cyclobutyl)-2-hydroxy-2-methylpropanamide | 420.3 |
| 67 | 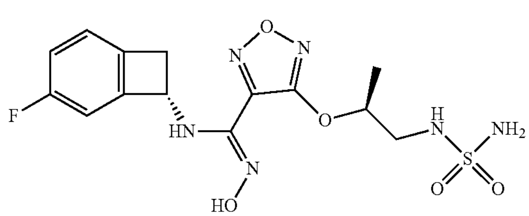 [SMILES: C[C@@H](CNS(N)(=O)=O)Oc1nonc1/C(=N/O)N[C@H]1Cc2ccc(F)cc21] | (Z)-N-((S)-4-fluorobicyclo[4.2.0]octa-1(6),2,4-trien-7-yl)-N'-hydroxy-4-(((S)-1-(sulfamoylamino)propan-2-yl)oxy)-1,2,5-oxadiazole-3-carboximidamide | 401.2 |

Biological Assays
IDO1 Enzyme Assay

Compounds to be tested were serially diluted in ten 3-fold steps in DMSO starting from 10 mM DMSO stocks. Compound dilutions or DMSO alone were then dispensed from the dilution plate into a Greiner black 384-well assay plate (catalog #781086) using an Echo 555 acoustic liquid handler (Labcyte).

HIS-tagged IDO1 protein was recombinantly expressed in *Escherichia coli* using ZYP5052 autoinduction media supplemented with 500 µM delta aminolevulinic acid for 48 hours at 16 degrees Celsius. IDO1 protein was purified using $Ni^{2+}$-affinity resin and size exclusion chromatography. Purified protein was then diluted in assay buffer (50 mM Tris pH 7.0, 1% glycerol, 20 µM methylene blue, 0.05% Tween-20, 20 mM sodium ascorbate, 100 units/mL catalase to obtain a final IDO1 concentration of 40 nM. IDO1 solution (30 µM) or buffer alone (30 µM) was dispensed to wells of the assay plate using a BioRAPTR liquid dispenser (Beckman Coulter). Assay plates containing compound and IDO1 enzyme were incubated at room temperature for 30 minutes. Afterwards, 10 µL of 400 µM tryptophan in assay buffer were added to each well of the assay plate using a BioRAPTR liquid dispenser. Plates were incubated at room temperature for 60 minutes and reactions were quenched by addition of 10 µL of 0.5 M methyl isonipecotate in dimethyl sulfoxide. Plates were sealed and incubated at 37 degrees Celsius for 4 hours or 50 degrees Celsius for 2 hours. The plates are allowed to cool and then centrifuged for 1 minute at 1000×g. The resulting fluorescence was measured in an Envision plate reader (Perkin Elmer) with a 400/25 nm excitation filter and an 510/20 nm emission filter.

The fluorescence intensity of each well was corrected for the background observed in wells that did not receive IDO 1 and was expressed as a fraction of the intensity observed in wells that received IDO1 enzyme and DMSO only. Potencies were calculated by linear least squares fit to the four parameter logistic IC50 equation.

IDO1 Cellular Assay in Hela Cells Stimulated with IFNγ

Hela cells were cultured in complete Hela culture medium (90% EMEM, 10% heat-inactivated fetal bovine serum) and expanded to about 1×109 cells. The cells were then collected and frozen down at 10×106 cells/vial in 1 mL frozen medium (90% complete Hela culture medium, 10% DMSO)

Compounds to be tested were serially diluted in ten 3-fold steps in DMSO starting from 10 mM DMSO stocks in Echo low volume plate(s). Compound dilutions or DMSO alone were then dispensed from the dilution plate(s) into Greiner black 384-well assay plate(s) (catalog #781086, 50 nL/well) using an Echo 550 acoustic liquid handler (Labcyte).

Frozen Hela cells were thawed and transferred into Hela assay medium (99% complete Hela culture medium, 1% Pen/Strep) with 20 mL medium/vial of cells. The cells were spun down at 250 g in a table top centrifuge for 5 min and suspended in same volume of Hela assay medium. The cells were then counted and adjusted to a density of 2×105 cells/ml in Hela assay medium. Sterile L-tryptophan were added to the cells with final concentration of 300 uM L-tryptophan. A small aliquot (2 mL/plate) of Hela cells were set aside and were not treated with IFNγ, to serve as the Max-E control. The rest of Hela cells were added with sterile IFNγ (Cat #285-IF, R & D systems) with a final concentration of 100 ng/mL.

Hela cells with and without IFNγ were dispensed to the respective wells of 384-well assay plates containing the compounds. The plates were incubated for about 48 hours at a 37° C., 5% $CO_2$ incubator. Afterwards, 12 µL of 0.5 M methyl isonipecotate in dimethyl sulfoxide were added into each well and the plates were sealed and incubated at 37° C. without $CO_2$ overnight. The plates were centrifuged for 1 min at 200×g. The resulting fluorescence was measured in a Spectramax plate reader (Molecular Devices) with a 400 nm excitation filter and a 510 nm emission filter.

The fluorescence intensity of each well was corrected for the background observed in wells with non-IFNγ-treated cells and was expressed as a fraction of the intensity observed in wells of IFNγ-treated cells and DMSO only. Potencies were calculated by linear least squares fit to the four parameter logistic $IC_{50}$ equation.

The biological activity data using the IDO1 enzyme assay and IDO1 cellular assay described above are summarized in the table below. Compounds disclosed herein generally have $IC_{50}$ of about 0.1 nM to about 20,000 nM, or more specifically, about 1 nM to about 10,000 nM, or more specifically, about 5 nM to about 5,000 nM, or more specifically, about 10 nM to about 1,000 nM, or still more specifically, about 10 nM to about 500 nM. Such a result is indicative of the intrinsic activity of the compounds in use as an inhibitor of an IDO enzyme. Specific $IC_{50}$ activity data for the exemplified compounds disclosed herein is provided in the following table.

| Ex. No. | IDO1 Enzyme Assay, $IC_{50}$, nM | IDO1 HELA Cell Assay, $IC_{50}$, nM |
|---|---|---|
| 1 | 49.34 | 106.5 |
| 2 | 75.65 | 93.48 |
| 3 | 58.5 | 51.39 |
| 4 | 139.2 | 323.5 |
| 5 | 113.6 | 321.7 |
| 6 | 48.3 | 58.26 |
| 7 | 72.05 | 88.64 |
| 8 | 109.6 | 416.1 |
| 9 | 413.3 | 623.5 |
| 10 | 100.3 | 334.9 |
| 11 | 74.83 | 194.2 |
| 12 | 700.2 | 920.1 |
| 13 | 483.4 | 774 |
| 14 | 985.1 | 769.6 |
| 15 | 479.4 | 684.7 |
| 16 | 446.7 | 509.1 |
| 17 | 185.9 | 220.5 |
| 18 | 74.73 | 300.6 |
| 19 | 7789 | 2851 |
| 20 | 302.2 | 2363 |
| 21 | 224.2 | 1783 |
| 22 | 264 | 307.7 |
| 23 | 1669 | 1926 |
| 24 | 420.7 | 1305 |
| 25 | 1205 | 1996 |
| 26 | 214.1 | 283.8 |
| 27 | 1483 | 1329 |
| 28 | 395.6 | 561.2 |
| 29 | 73.1 | 146.8 |
| 30 | 55.99 | 65.93 |
| 31 | 746.6 | 749.7 |
| 32 | 308 | 340.4 |
| 33 | 39.78 | 53.05 |
| 34 | 289.2 | 870.3 |
| 35 | 2146 | 2026 |
| 36 | 50.72 | 42.11 |
| 37 | 83.39 | 91.29 |
| 38 | 67.82 | 74.95 |
| 39 | 334.3 | 446.2 |
| 40 | 2381 | 1035 |
| 41 | 140.8 | 180.8 |
| 42 | 48.95 | 40.02 |
| 43 | 36.6 | 45.41 |
| 44 | 866.3 | 1313 |
| 45 | 990.2 | 1285 |
| 46 | 2454 | 1644 |
| 47 | 56.58 | 49.9 |

-continued

| Ex. No. | IDO1 Enzyme Assay, IC$_{50}$, nM | IDO1 HELA Cell Assay, IC$_{50}$, nM |
|---|---|---|
| 48 | 101.6 | 88.37 |
| 49 | 10720 | 7309 |
| 50 | 516.4 | 822.3 |
| 51 | 1070 | 1342 |
| 52 | 1810 | 1294 |
| 53 | 215.5 | 328.3 |
| 54 | 1493 | 1338 |
| 55 | 215.5 | 328.3 |
| 56 | 1493 | 1338 |
| 57 | 215.5 | 328.3 |
| 58 | 1493 | 1338 |
| 59 | 364.3 | 298.2 |
| 60 | 1386 | 1441 |
| 61 | 89 | 99 |
| 62 | 24 | 44 |
| 63 | 20 | 36 |
| 64 | 37 | 66 |
| 65 | 167 | 280 |
| 66 | 167 | 287 |
| 67 | 1551 | 848 |

IDO1 Human Whole Blood Assay

Compounds to be tested were serially diluted in ten 3-fold steps in DMSO starting from 10 mM. 3 µL of compound dilutions or DMSO alone were then dispensed from the dilution plate into a polypropylene 96-well assay plate containing 97 µL of RPMI using an Echo 555 acoustic liquid handler (Labcyte). LPS and IFNγ was prepared in RPMI to a 10× of final conc. (1000 ng/mL), final concentration is 100 ng/mL.

Human whole blood was drawn in sodium heparin coated tubes from healthy internal donors. Two hundred forty µL of blood was transferred to each of the wells of a v-bottom 96 well plate. Thirty µL of compound was transferred from intermediate dilution plate, and incubated for 15 min. Thirty µL from stimulants was then transferred to blood and mixed thoroughly. Plate was covered with breathable membrane and incubated at 37° C. for overnight (18 h).

On day 2 isotope labeled standard of kynurenine and tryptophan was made in water at 10× concentration and 30 µL was added to the blood at 3 µM final concentration. The assay plates were centrifuged at 300×G for 10 min with no brake to separate plasma from red blood cells. Sixty µL of plasma samples was removed without disturbing red blood cells. Plasma was diluted with RPMI in 1:1 ratio and proteins were precipitated out with two volume of Acetonitrile. The plates was centrifuged at 4000×G for 60 min. Twenty µL of supernatant was carefully transferred to a 384 well plate contain 40 µL of 0.1% formic acid in water and analyzed by LC/MS/MS.

LC/MS/MS analyses were performed using Thermo Fisher's LX4-TSQ Quantum Ultra system. This system consists of four Agilent binary high-performance liquid chromatography (HPLC) pumps and a TSQ Quantum Ultra triple quadruple MS/MS instrument. For each sample, 5 µL were injected onto an Atlantis T3 column (2.1 mm×150 mm, 3 µm particle size) from Waters. The mobile phase gradient pumped at 0.8 mL/min was used to elute the analytes from the column at 25° C. The elution started at 0% B increasing linearly to 25% B at 6.5 min, holding at 25% for 1 min, re-equilibrating to 10 min. Mobile phase A consisted of 0.1% formic acid in water. Mobile phase B consisted of 0.1% of formic acid in acetonitrile. Data was acquired in positive mode using a HESI interface. The operational parameters for the TSQ Quantum Ultra instrument were a spray voltage of 4000 V, capillary temperature of 380° C., vaporizer temperature 400° C., shealth gas 60 arbitrary units, Aux gas 20 arbitrary units, tube lens 85 and collision gas 1.2 mTorr. SRM chromatograms of kynurenine (Q 1: 209.2>Q3:94.0) and internal standard (Q1: 215.3>Q3:98.2) were collected for 90 sec. The peak area was integrated by Xcalibur Quan software. The ratios between the kynurenine generated in the reaction and 2D6-Kynurenine spiked-in internal standard were used to generate percentage inhibition and IC$_{50}$ values. Compounds were titrated and IC$_{50}$'s were calculated by 4 parameter sigmoidal curve fitting formula.

The biological activity data of selective compounds using the IDO 1 human whole blood assay described above are summarized in the table below.

| Ex. No. | IDO1 human whole blood assay, IC$_{50}$, nM |
|---|---|
| 1 | 666.4 |
| 2 | 232.5 |
| 3 | 185.4 |
| 4 | 1414 |
| 5 | 714.9 |
| 6 | 351.3 |
| 7 | 1176 |
| 11 | 262.4 |
| 30 | 665.5 |
| 33 | 503.3 |
| 36 | 314.2 |
| 38 | 518.6 |
| 42 | 387.6 |
| 43 | 1440 |
| 47 | 500.6 |
| 48 | 400.3 |
| 56 | 386.1 |
| 57 | 954.9 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of formula (I), or a pharmaceutically acceptable salt thereof:

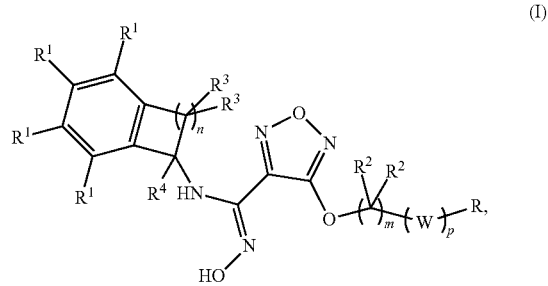

(I)

wherein:
m is 0, 1, 2, 3 or 4; is 1, 2, or 3; p is 0, 1, 2 or 3;
W is selected from (a) —CR$^a$R$^b$— and (b) —NR$^a$—;
wherein each R$^a$ and R$^b$ is independently selected from the group consisting of (a) hydrogen, (b) halogen and (c) C$_{1-6}$ alkyl, optionally substituted with —OH or halogen;
R is selected from the group consisting of:
(a) hydrogen;
(b) C$_{1-6}$alkyl, optionally substituted with one to three substituents independently selected from the group consisting of (i) —OH, (ii) halogen, and (iii) —NH$_2$;

(c) $C_{3-6}$cycloalkyl, optionally substituted with one to three substituents independently selected from the group consisting of (i) —OH and (ii) —$C_{1-6}$alkyl, optionally substituted with —OH;

(d) —(C=O)—(NH)$_q$—R$^c$, wherein q is 0 or 1; and R$^c$ is selected from the group consisting of:
  (i) hydrogen,
  (ii) —$C_{1-6}$alkyl, optionally substituted with one to three substituents independently selected from the group consisting of (1) halogen, (2) —OH, (3) —O-methyl, (4) —$C_{3-6}$cycloalkyl, (5) —CN, (6) —S(O)$_2$-$C_{1-6}$alkyl and (7) heterocyclyl,
  (iii) —O-$C_{1-6}$alkyl,
  (iv) —OH,
  (v) —$C_{3-6}$cycloalkyl, optionally substituted with —OH or —$C_{1-6}$alkyl, and
  (vi) a 4-, 5- or 6-membered heterocyclyl, optionally substituted with one to four substituents independently selected from the group consisting of (1) halogen, (2) $C_{1-6}$alkyl and (3) —OH;

(e) —S(O)$_2$—NR$^d$R$^e$; each of R$^d$ and R$^e$ is independently hydrogen or $C_{1-6}$alkyl;

(f) —S(O)$_2$—$C_{1-6}$alkyl;

(g) $C_{4-5}$cycloalkenyl, optionally substituted with one to four substituents independently selected from the group consisting of (i) oxo, (ii) —$C_{1-6}$alkyl and (iii) —NH—$C_{1-6}$alkyl; and (h) a 4-, 5- or 6-membered heterocyclyl, optionally substituted with one to four substituents independently selected from the group consisting of (i) halogen, (ii) $C_{1-6}$alkyl, (iii) oxo and (iv) —C(O)—$C_{1-6}$alkyl, optionally substituted with —OH;

each occurrence of R$^1$ is independently selected from the group consisting of (a) hydrogen, (b) halogen, (c) —CN, (d) $C_{1-6}$ alkyl, optionally substituted with 1 to 3 halogens, and (e) —O—$C_{1-6}$alkyl, optionally substituted with one to three halogens;

each occurrence of R$^2$ is independently selected from the group consisting of (a) hydrogen, (b) halogen, (c) —OH and (d) $C_{1-6}$alkyl, optionally substituted with —OH;

or, alternatively, two R$^2$ groups together with the carbon to which they are attached form a $C_{3-6}$ cycloalkyl or 4-, 5-, or 6-membered heterocycle;

or, alternatively, R$^2$ and R$^a$ of W together with the carbon and/or nitrogen atoms to which they are attached form a 4-, 5- or 6-membered carbocycle or heterocycle;

each occurrence of R$^3$ is independently selected from the group consisting of (a) hydrogen, (b) halogen, (c) $C_{1-6}$ alkyl and (d) —O—$C_{1-6}$ alkyl; and R$^4$ is selected from the group consisting of (a) hydrogen and (b) $C_{1-6}$ alkyl.

2. The compound of claim 1, or a pharmaceutically acceptable salt thereof,
wherein m is 1 or 2; n is 1 or 2; and p is 0, 1 or 2;
W is selected from (a) —CR$^a$R$^b$— and (b) —NR$^a$—;
wherein each occurrence of R$^a$ and R$^b$ is independently selected from the group consisting of (a) hydrogen and (b) $C_{1-6}$ alkyl, optionally substituted with —OH;
R is selected from the group consisting of:
(a) hydrogen;
(b) $C_{1-6}$alkyl, optionally substituted with one to three substituents independently selected from the group consisting of (i) —OH and (ii) halogen;
(c) $C_{3-6}$cycloalkyl, optionally substituted with —OH;

(d) —(C=O)—(NH)$_q$—R$^c$, wherein q is 0 or 1; and R$^c$ is selected from the group consisting of:
  (i) hydrogen,
  (ii) —$C_{1-6}$alkyl, optionally substituted with one to three substituents independently selected from the group consisting of (1) halogen, (2) —OH, (3) —O—methyl and (4) —$C_{3-6}$cycloalkyl,
  (iii) —O—$C_{1-6}$alkyl, and
  (iv) a 5- or 6-membered heterocyclyl, optionally substituted with one to four substituents independently selected from the group consisting of (1) halogen, (2) $C_{1-6}$alkyl and (3) —OH;

(e) —S(O)$_2$—NH$_2$;

(f) —S(O)$_2$—$C_{1-6}$alkyl; and (g) a 4-, 5- or 6-membered heterocyclyl, optionally substituted with one to four substituents independently selected from the group consisting of (i) halogen, (ii) $C_{1-6}$alkyl, (iii) oxo and (iv) —C(O)—$C_{1-6}$alkyl, optionally substituted with —OH;

each occurrence of R$^1$ is independently selected from the group consisting of (a) hydrogen, (b) halogen, and (c) —CN;

each occurrence of R$^2$ is independently selected from the group consisting of (a) hydrogen and (b) —OH;

or alternatively, two R$^2$ groups together with the carbon to which they are attached form a $C_{3-6}$ cycloalkyl or a 4-, 5-, or 6-membered heterocycle;

or alternatively, R$^2$ and R$^a$ of W together with the carbon and/or nitrogen atoms to which they are attached form a 4-, 5- or 6-membered carbocycle or heterocycle;

each occurrence of R$^3$ is independently selected from the group consisting of (a) hydrogen and (b) $C_{1-6}$ alkyl; and R$^4$ is selected from the group consisting of (a) hydrogen and (b) $C_{1-6}$ alkyl.

3. The compound of claim 1, or a pharmaceutically acceptable salt thereof, wherein:
R is selected from the group consisting of:
(a) hydrogen;
(b) $C_{1-6}$alkyl, optionally substituted with one to three —OH;
(c) $C_{3-6}$cycloalkyl, optionally substituted with —OH;
(d) —(C=O)—(NH)$_q$—R$^c$, wherein q is 0 or 1; and R$^c$ is selected from the group consisting of:
  (i) hydrogen,
  (ii) —$C_{1-6}$alkyl, optionally substituted with one to three —OH,
  (iii) —O—$C_{1-6}$alkyl, and
  (iv) a 5- or 6-membered heterocyclyl, optionally substituted with one to four substituents independently selected from the group consisting of (1) halogen, (2) $C_{1-6}$alkyl and (3) —OH;
(e) —S(O)$_2$—NH$_2$;
(f) —S(O)$_2$—$C_{1-4}$alkyl; and
(g) a 5- or 6-membered heterocyclyl, optionally substituted with one to four substituents independently selected from the group consisting of (i) halogen, (ii) $C_{1-6}$alkyl and (iii) oxo; and each occurrence of R$^a$ and R$^b$ is independently selected from the group consisting of (a) hydrogen and (b) $C_{1-4}$ alkyl, optionally substituted with —OH.

4. The compound of claim 1, or a pharmaceutically acceptable salt thereof, wherein R is a 5- or 6-membered heterocyclyl selected from the group consisting of pyridinyl, pyrimidinyl, piperidinyl, pyrrolidinyl, triazolyl and thiazolyl;
wherein the 5- or 6-membered heterocyclyl is optionally substituted with one to four substituents independently selected from the group consisting of (i) $C_{1-6}$alkyl and (ii) oxo.

5. The compound of claim 1, or a pharmaceutically acceptable salt thereof, wherein each occurrence of $R^1$ is independently selected from the group consisting of (a) hydrogen and (b) halogen.

6. The compound of claim 1, or a pharmaceutically acceptable salt thereof, wherein each occurrence of $R^2$ is independently selected from the group consisting of (a) hydrogen and (b) —OH.

7. The compound of claim 1, or a pharmaceutically acceptable salt thereof, wherein each occurrence of $R^3$ is independently selected from the group consisting of (a) hydrogen and (b) $C_{1-4}$ alkyl.

8. The compound of claim 1, or a pharmaceutically acceptable salt thereof, wherein m is 1 or 2; n is 1; and p is 0, 1 or 2;

W is selected from (a) —$CR^aR^b$— and (b) —$NR^a$—; wherein each occurrence of $R^a$ and $R^b$ is independently selected from the group consisting of (i) hydrogen and (ii) $C_{1-4}$alkyl;

R is selected from the group consisting of:
(a) hydrogen;
(b) $C_{1-6}$alkyl, optionally substituted with one to three —OH;
(c) $C_{3-6}$cycloalkyl, optionally substituted with —OH;
(d) —(C=O)—(NH)$_q$—$R^c$, wherein q is 0 or 1; and $R^c$ is selected from the group consisting of:
  (i) hydrogen,
  (ii) —$C_{1-6}$alkyl, optionally substituted with one to three —OH,
  (iii) —O—$C_{1-6}$alkyl, and
  (iv) a 5- or 6-membered heterocyclyl selected from the group consisting of pyridinyl, pyrimidinyl, piperidinyl, triazolyl and thiazolyl;
(e) —$S(O)_2$—$NH_2$;
(f) —$S(O)_2$—$C_{1-4}$alkyl; and
(g) a 5- or 6-membered heterocyclyl selected from the group consisting of pyridinyl, pyrimidinyl, piperidinyl, pyrrolidinyl, triazolyl and thiazolyl;

each occurrence of $R^1$ is independently selected from the group consisting of (a) hydrogen and (b) halogen;

each occurrence of $R^2$ is independently selected from the group consisting of (a) hydrogen and (b) —OH;

or alternatively, two $R^2$ groups together with the carbon to which they are attached form a $C_{3-6}$ cycloalkyl or 4-, 5-, or 6-membered heterocycle;

or alternatively, $R^2$ and $R^a$ of W together with the carbon and/or nitrogen atoms to which they are attached form a 4-, 5- or 6-membered carbocycle or heterocycle;

each occurrence of $R^3$ is hydrogen; and $R^4$ is selected from the group consisting of (a) hydrogen and (b) $C_{1-4}$ alkyl.

9. The compound of claim 1 having formula (Ia), or a pharmaceutically acceptable salt thereof:

(Ia)

wherein: m is 1, 2, or 3; n is 1 or 2; p is 0 or 1;

R is selected from the group consisting of:
(a) $C_{1-6}$alkyl, optionally substituted with one to three substituents independently selected from the group consisting of (i) —OH and (ii) halogen,
(b) $C_{3-6}$cycloalkyl, optionally substituted with —OH,
(c) —(C=O)—(NH)$_q$—$R^c$, wherein q is 0 or 1; and $R^c$ is selected from the group consisting of:
  (i) hydrogen,
  (ii) —$C_{1-6}$alkyl, optionally substituted with one to three substituents independently selected from the group consisting of (1) halogen, (2) —OH and (3) heterocyclyl,
  (iii) —O—$C_{1-6}$alkyl,
  (iv) —$C_{3-6}$cycloalkyl, optionally substituted with —OH, and
  (v) a 5- or 6-membered heterocyclyl, optionally substituted with one to four substituents independently selected from the group consisting of (1) halogen, (2) $C_{1-6}$alkyl and (3) —OH;
(d) —$S(O)_2$—$NR^dR^e$; each of $R^d$ and $R^e$ W is independently hydrogen or $C_{1-6}$alkyl;
(e) —$S(O)_2$—$C_{1-6}$alkyl; and
(f) a 5- or 6-membered heterocyclyl, optionally substituted with one to four substituents independently selected from the group consisting of (i) halogen and (ii) $C_{1-6}$alkyl;

$R^a$ is selected from the group consisting of (a) hydrogen and (b) $C^{1-6}$ alkyl, optionally substituted with —OH, each occurrence of $R^1$ is independently selected from the group consisting of (a) hydrogen, (b) halogen and (c) $C_{1-6}$alkyl;

each occurrence of $R^2$ is independently selected from the group consisting of (a) hydrogen, (b) —OH and (c) $C_{1-6}$alkyl, optionally substituted with —OH; and each occurrence of $R^3$ is independently selected from the group consisting of (a) hydrogen and (b) $C_{1-6}$alkyl.

10. The compound of claim 9, or a pharmaceutically acceptable salt thereof, wherein: m is 1 or 2; n is 1; p is 0 or 1;

R is selected from the group consisting of:
(a) $C_{1-6}$alkyl, optionally substituted with one to three substituents independently selected from the group consisting of (i) —OH and (ii) halogen,
(b) —(C=O)—(NH)$_q$—$R^c$, wherein q is 0 or 1; and $R^c$ is selected from the group consisting of:
  (i) hydrogen,
  (ii) —$C_{1-6}$alkyl, optionally substituted with one to three substituents independently selected from the group consisting of (1) halogen and (2) —OH,
  (iii) —$C_{3-6}$cycloalkyl, optionally substituted with —OH, and
  (iv) a 5- or 6-membered heterocyclyl, optionally substituted with one to four substituents independently selected from the group consisting of (1) halogen, (2) $C_{1-6}$alkyl and (3) —OH;
(c) —$S(O)_2$—$NH_2$;
(d) —$S(O)_2$—$C_{1-6}$alkyl; and
(e) a 5- or 6-membered heterocyclyl selected from pyridinyl, pyrimidinyl, piperidinyl, triazolyl, and thiazolyl;

$R^a$ is selected from the group consisting of (a) hydrogen and (b) $C_{1-4}$ alkyl, optionally substituted with —OH;

each occurrence of $R^1$ is independently selected from the group consisting of (a) hydrogen, (b) halogen and (c) $C_{1-4}$ alkyl;

each occurrence of $R^2$ is independently selected from the group consisting of (a) hydrogen, (b) —OH and (c) $C_{1-4}$alkyl, optionally substituted with —OH; and each occurrence of $R^3$ is independently selected from the group consisting of (a) hydrogen and (b) $C_{1-4}$alkyl.

11. The compound of claim 9 having formula (Ib), or a pharmaceutically acceptable salt thereof,

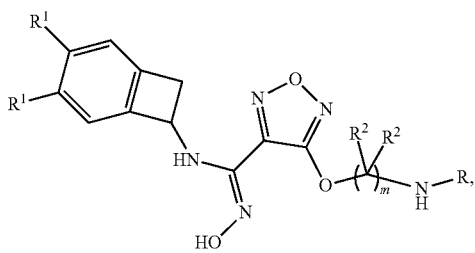

(Ib)

wherein: m is 1 or 2;

R is selected from the group consisting of:
(a) —(C=O)—(NH)$_q$—$R^c$, wherein q is 0 or 1; and $R^c$ is selected from the group consisting of:
   (i) hydrogen,
   (ii) —$C_{1-4}$alkyl, optionally substituted with one to two —OH,
   (iii) —$C_{3-6}$cycloalkyl, optionally substituted with —OH; and
(b) —S(O)$_2$—NH$_2$; and
(c) —S(O)$_2$—$C_{1-4}$alkyl;

each occurrence of $R^1$ is independently selected from the group consisting of (a) hydrogen and (b) halogen; and each occurrence of $R^2$ is independently selected from the group consisting of (a) hydrogen and (b) —OH.

12. The compound of claim 11, or a pharmaceutically acceptable salt thereof, wherein: m is 2;

R is selected from the group consisting of: (a) —S(O)$_2$—NH$_2$, (b) —S(O)$_2$—CH$_3$, (c) —S(O)$_2$—CH$_2$CH$_3$ and (d) —S(O)$_2$—CH$_2$CH$_2$CH$_3$ $R^1$ is selected from the group consisting of (a) hydrogen, (b) —F and (c) —Cl; and each occurrence of $R^2$ is hydrogen.

13. The compound of claim 1 having formula (Ic), or a pharmaceutically acceptable salt thereof:

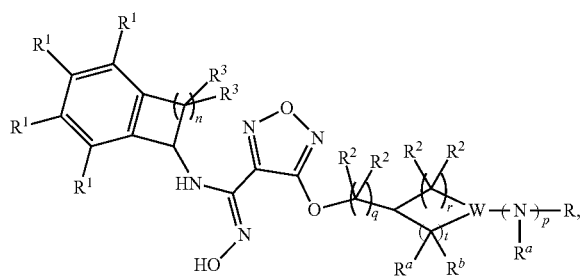

(Ic)

wherein: n is 1 or 2; p is 0 or 1; q is 0, 1 or 2; r is 1 or 2; t is 0, 1 or 2;

W is N or $CR^a$; provided when W is N, p is 0;
R is selected from the group consisting of:
(a) hydrogen,
(b) —(C=O)—$R^c$, wherein $R^c$ is selected from the group consisting of:
   (i) hydrogen,
   (ii) —$C_{1-6}$alkyl, optionally substituted with one to three substituents independently selected from the group consisting of (1) halogen and (2) —OH,
   (iii) —O—$C_{1-6}$alkyl, and
   (iv) a 5- or 6-membered heterocyclyl, optionally substituted with one to four substituents independently selected from the group consisting of (1) halogen, (2) $C_{1-6}$alkyl and (3) —OH;
(c) —S(O)$_2$—NR$^d$R$^e$; each of R$^d$ and R$^e$ is independently hydrogen or $C_{1-6}$alkyl; and
(d) —S(O)$_2$—$C_{1-6}$alkyl;

each occurrence of $R^a$ and $R^b$ is independently selected from the group consisting of (a) hydrogen and (b) $C_{1-6}$ alkyl, optionally substituted with —OH;

each occurrence of $R^1$ is independently selected from the group consisting of (a) hydrogen and (b) halogen;

each occurrence of $R^2$ is independently selected from the group consisting of (a) hydrogen and (b) —OH; and each occurrence of $R^3$ is independently selected from the group consisting of (a) hydrogen and (b) $C_{1-6}$alkyl.

14. The compound of claim 13, or a pharmaceutically acceptable salt thereof:

wherein: n is 1 or 2; p is 0 or 1; q is 0; r is 1 or 2; t is 0, 1 or 2;

W is N or $CR^a$; provided when W is N, p is 0;
R is selected from the group consisting of:
(a) hydrogen,
(b) —(C=O)—$R^c$, wherein $R^c$ is selected from the group consisting of:
   (i) hydrogen,
   (ii) —$C_{1-6}$alkyl, optionally substituted with one to three substituents independently selected from the group consisting of (1) halogen and (2) —OH,
   (iii) —O—$C_{1-6}$alkyl, and
   (iv) a 5- or 6-membered heterocyclyl selected from pyridinyl, pyrimidinyl, piperidinyl, pyrrolidinyl, triazolyl and thiazolyl;
(c) —S(O)$_2$—NH$_2$; and
(d) —S(O)$_2$—$C_{1-4}$alkyl;

each occurrence of $R^a$ and $R^b$ is hydrogen;

each occurrence of $R^1$ is independently selected from the group consisting of (a) hydrogen and (b) halogen;

each occurrence of $R^2$ is independently selected from the group consisting of (a) hydrogen and (b) —OH; and each occurrence of $R^3$ is hydrogen.

15. The compound of claim 13 having formula (Id), or a pharmaceutically acceptable salt thereof,

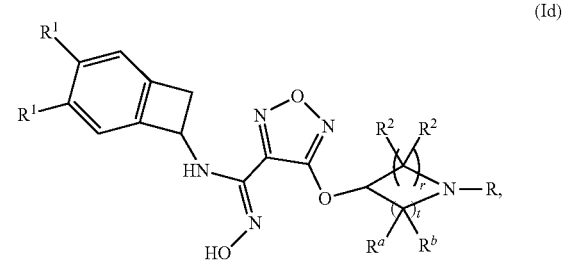

(Id)

wherein: r is 1 or 2; t is 1 or 2;
R is selected from the group consisting of:
(a) hydrogen;
(b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and
  (iv) a 5- or 6-membered heterocyclyl selected from pyridinyl, pyrimidinyl, piperidinyl, pyrrolidinyl, triazolyl and thiazolyl;
(c) —S(O)$_2$—NH$_2$; and
(d) —S(O)$_2$—C$_{1-4}$alkyl;
each occurrence of R$^a$ and R$^b$ is independently selected from the group consisting of (a) hydrogen and (b) C$_{1-4}$alkyl;
each occurrence of R$^1$ is independently selected from the group consisting of (a) hydrogen and (b) halogen; and
each occurrence of R$^2$ is independently selected from the group consisting of (a) hydrogen and (b) —OH.

16. The compound of claim 13 having formula (Ie), or a pharmaceutically acceptable salt thereof, (Ie)

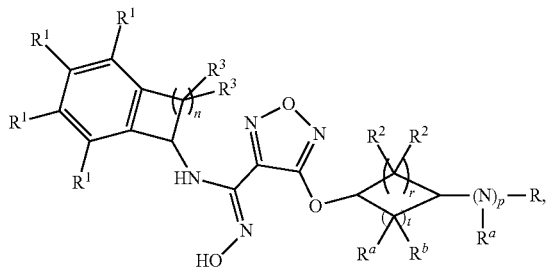

wherein: n is 1 or 2; p is 0 or 1; r is 1 or 2; t is 0, 1 or 2;
R is selected from the group consisting of:
(a) hydrogen,
(b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and
  (iv) a 5- or 6-membered heterocyclyl, optionally substituted with one to four substituents independently selected from the group consisting of (1) halogen, (2) C$_{1-6}$alkyl and (3) —OH;
(c) —S(O)$_2$—NR$^d$R$^e$; each of R$^d$ and R$^e$ is independently hydrogen or C$_{1-6}$alkyl; and
(d) —S(O)$_2$—C$_{1-6}$alkyl;
each occurrence of R$^a$ and R$^b$ is independently selected from the group consisting of (a) hydrogen and (b) C$_{1-6}$ alkyl, optionally substituted with —OH;
each occurrence of R$^1$ is independently selected from the group consisting of (a) hydrogen and (b) halogen;
each occurrence of R$^2$ is independently selected from the group consisting of (a) hydrogen and (b) —OH; and
each occurrence of R$^3$ is independently selected from the group consisting of (a) hydrogen and (b) C$_{1-6}$alkyl.

17. The compound of claim 16 having formula (If), or a pharmaceutically acceptable salt thereof, (If)

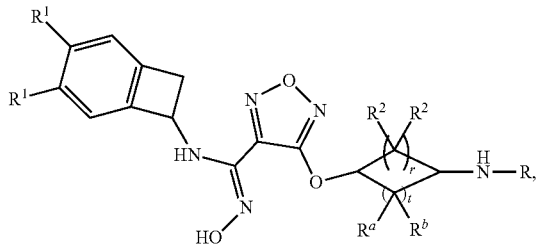

wherein: r is 1 or 2; t is 0, 1 or 2;
R is selected from the group consisting of:
(a) hydrogen,
(b) —(C=O)—R$^c$, wherein R$^c$ is selected from the group consisting of:
  (i) hydrogen,
  (ii) —C$_{1-6}$alkyl, optionally substituted with one to three substituents independently selected from the group consisting of (1) halogen and (2) —OH,
  (iii) —O—C$_{1-6}$alkyl, and
  (iv) a 5- or 6-membered heterocyclyl selected from pyridinyl, pyrimidinyl, piperidinyl, pyrrolidinyl, triazolyl and thiazolyl;
(c) —S(O)$_2$—NH$_2$; and
(d) —S(O)$_2$—C$_{1-6}$alkyl;
each occurrence of R$^a$ and R$^b$ is hydrogen;
each occurrence of R$^1$ is independently selected from the group consisting of (a) hydrogen and (b) halogen; and
each occurrence of R$^2$ is hydrogen.

18. The compound of claim 1, or a pharmaceutically acceptable salt thereof, selected from the group consisting of:
(S)—N—(4—fluorobicyclo[4.2.0]octa—1(6),2,4—trien—7—yl)—N'—hydroxy—4—(2—(sulfamoylamino)ethoxy) —1,2,5—oxadiazole—3—carboximidamide,
(S)—N—(4—fluorobicyclo[4.2.0]octa—1(6),2,4—trien—7—yl)—N'—hydroxy—4—((1—(2—hydroxyacetyl)azetidin—3—yl)oxy)—1,2,5—oxadiazole—3—carboximidamide,
(S)—N—(2—((4—(N—(4—fluorobicyclo[4.2.0]octa—1(6),2,4—trien—7—yl)—N'—hydroxycarbamimidoyl)—1,2,5—oxadiazol—3—yl)oxy)ethyl)acetamide,
(S)—2—((4—(N—(4—fluorobicyclo[4.2.0]octa-1(6),2,4—trien—7—yl)—N'—hydroxycarbamimidoyl)—1,2,5—oxadiazol—3—yl)oxy)—N—(2—hydroxyethyl)acetamide,
N—{2—[(4—{N—[(7 S)—4—fluorobicyclo[4.2.0]octa—1,3,5—trien—7—yl]—N'—hydroxycarbamimidoyl}—1,2,5—oxadiazol—3 —yl)oxy]ethyl}—2—hydroxyacetamide,
N—[(7S)—4—fluorobicyclo[4.2.0]octa—1,3,5—trien—7—yl]—N'—hydroxy—4—{2—[(methylsulfonyl)amino]ethoxy}—1,2,5 —oxadiazole—3 —carboximidamide,
2—[(4—{N—[(7S)—4—fluorobicyclo[4.2.0]octa—1,3,5—trien—7—yl]—N'—hydroxycarbamimidoyl}—1,2,5—oxadiazol—3 —yl)oxy]—N—[(2 S)—1—hydroxypropan—2—yl]acetamide,
2—[(4—{N—[(7S)—4—fluorobicyclo[4.2.0]octa—1,3,5—trien—7—yl]—N'—hydroxycarbamimidoyl}—1,2,5—oxadiazol—3 —yl)oxy]—N—[(2R)—1—hydroxypropan—2—yl]acetamide,
2—[(4—{N—[(7S)—4—fluorobicyclo[4.2.0]octa—1,3,5—trien—7—yl]—N'—hydroxycarbamimidoyl}—1,2,5—oxadiazol—3 —yl)oxy]—N—[(2 S)—2—hydroxypropyl]acetamide, 2—[(4—{N—(7S)—4—fluorobicyclo[4.2.0]octa—1,3,5—trien—7—yl]—N'—hydroxycarbamimidoyl}—1,2,5—oxadiazol—3—yl)oxy]—N—[(2R)—2—hydroxypropyl]acetamid, 4—[2—(carbamoylamino)ethoxy]—N—(4—fluorobicyclo[4.2.0]octa—1,3,5—trien—7—yl)—N'—hydroxy—1,2,5—oxadiazole—3—carboximidamide, N—(2,3—dihydroxypropyl)—2—({4—[N—(4—fluorobicyclo[4.2.0]octa—1,3,5—trien—7—yl)—N'—hydroxycarbamimidoyl]—1,2,5—oxadiazol—3—yl}oxy)acetamide, 2—[(4—{N—[(1S)—6—fluoro13 2,3—dihydro—1H—inden—1—yl]—N'—hydroxycarbamimidoyl}—1,2,5—oxadiazol—3—yl)oxy]—N—(2—hydroxyethyl)acetamide, 2—({4[N—(4—fluorobicyclo[4.2.0]octa—1,3,5—trien—7—yl)—N'—hydroxycarbamimidoyl]—1,2,5—oxadiazol—3—yl}oxy)—N—(2—hydroxy—2—methylpropyl)acetamide, 4—{2—[carbamoyl(2—hydroxyethyl)amino]ethoxy}—N—(4—fluorobicyclo[4.2.0]octa—1,3,5—trien—7—yl)—N'—hydroxy—1,2,5—oxadiazole—3—carboximidamide, N—[(2R)—2,3—dihydroxypropyl]—2—[(4—{N—[(7S)—4—fluorobicyclo[4.2.0]octa—1,3,5—trien—7—yl]—N'—hydroxycarbamimidoyl}—1,2,5—oxadiazol—3—yl)oxy]acetamide, 2—[(4—{N—[7S]—4—fluorobicyclo[4.2.0]octa—1,3,5—trien—7—yl]—N'—hydroxycarbamimidoyl}—1,2,5—oxadiazol—3—yl)oxy]acetamide, 4{(carbamoylamino)propoxy]—N—[(7S)—4—fluorobicyclo[4.2.0]octa—1,3,5—trien—7—yl]—N'—hydroxy—1,2,5—oxadiazole—3—carboximidamide, 2—({4[N—(4—fluorobicyclo[4.2.0]octa—1,3,5—trien—7—yl)—N'—hydroxycarbamimidoyl]—1,2,5—oxadiazol—3—yl}oxy)—N—(2—hydroxyethyl)—2—methylpropanamide, (2R)—N—{2—[(4—{N—[7S]—4—fluorobicyclo[4.2.0]octa—1,3,5—trien—7—yl]—N'—hydroxycarbamimidoyl}—1,2,5—oxadiazol—3—yl)oxy]ethyl}—2,3—dihydroxypropanamide, 4—[(azetidin—3—yl)oxy]—N—[(7S)—4—fluorobicyclo[4.2.0]octa—1,3,5—trien—7—yl]—N'—hydroxy—1,2,5—oxadiazole—3—carboximidamide, N—{2—[(4—{N—[(7S)—4—fluorobicyclo[4.2.0]octa—1,3,5—trien—7—yl]—N'—hydroxycarbamimidoyl}—1,2,5—oxadiazol—3—yl)oxy]ethyl}—1H—1,2,4—triazole—3—carboxamide, 2—({44[N—(4—fluorobicyclo[4.2.0]octa—1,3,5—trien—7—yl)—N'—hydroxycarbamimidoyl]—1,2,5—oxadiazol—3—yl}oxy)—N—(2—hydroxyethyl)propanamide, N—[(1S)—6—fluoro—2,3—dihydro—1H—inden—1—yl]—N'—hydroxy—4—[2—(sulfamoylamino)ethoxy]—1,2,5—oxadiazole—3—carboximidamide, N—[(7S)—4—fluorobicyclo[4.2.0]octa—1,3,5—trien—7—yl]—N'—hydroxy—4—{[(3S)—1—(hydroxyacetyl)pyrrolidin—3—yl]oxy}—1,2,5—oxadiazole—3—carboximidamide, (2S)—N—{2—[(4—{N—[(7S)—4—fluorobicyclo[4.2.0]octa—1,3,5—trien—7—yl]—N'—hydroxycarbamimidoyl}—1,2,5—oxadiazol—3—yl)oxy]ethyl}—2,3—dihydroxypropanamide, N—[(7S)—4—fluorobicyclo[4.2.0]octa—1,3,5—trien—7—yl]—N'—hydroxy—4—[2-(methylsulfonyl)ethoxy]—1,2,5—oxadiazole—3—carboximidamide, N—[(7S)—4—fluorobicyclo[4.2.0]octa—1,3,5—trien—7—yl]—N'—hydroxy—4—[2—(4H—1,2,4—triazol—4—yl)ethoxy]—1,2,5—oxadiazole—3—carboximidamide, N—[(7S)—4—fluorobicyclo[4.2.0]octa—1,3,5—trien—7—yl]—N'—hydroxy—4—(3—sulfamoylpropoxy)—1,2,5—oxadiazole—3—carboximidamide, N—[(7S)—4—fluorobicyclo[4.2.0]octa—1,3,5—trien—7—yl]—N'—hydroxy—4—{[1—(1H—1,2,4—triazole—3—carbonyl)azetidin—3—yl]oxy}—1,2,5—oxadiazole—3—carboximidamide, N—[(7S)—4—fluorobicyclo[4.2.0]octa—1,3,5—trien—7—yl]—N'—hydroxy—4—{[(3R)1—sulfamoylpyrrolidin—3—yl]oxy}—1,2,5—oxadiazole—3—carboximidamide, N—[(7S)—4—fluorobicyclo[4.2.0]octa—1,3,5—trien—7—yl]—N'—hydroxy—4—{[(3S)—1—sulfamoylpyrrolidin—3—yl]oxy}—1,2,5—oxadiazole—3—carboximidamide, N—{2—[(4—{N—[7S]—4—fluorobicyclo[4.2.0]octa—1,3,5—trien—7—yl]—N'—hydroxycarbamimidoyl}—1,2,5—oxadiazol—3—yl)oxy]ethyl}propanamide, N—[(7S)—4—fluorobicyclo[4.2.0]octa—1,3,5—trien—7—yl]—N'—hydroxy—4—(2—sulfamoylethoxy)—1,2,5—oxadiazole—3—carboximidamide, N—{1—[(4—{N—[(7S)—4—fluorobicyclo[4.2.0]—1,3,5—trien—7—yl]—N'—hydroxycarbamimidoyl}—1,2,5—oxadiazol—3—yl)oxy]—2—methylpropan—2—yl}—2—hydroxyacetamide, N—{cis—3—[(4—{N—[(7S)—4—fluorobicyclo[4.2.0]octa—1,3,5—trien—7—yl]—N'—hydroxycarbamimidoyl}—1,2,5—oxadiazol—3—yl)oxy]cyclobutyl}acetamide, N—{trans—3—[(4—{N—[(7S)—4—fluorobicyclo[4.2.0]octa—1,3,5—trien—7—yl]—N'—hydroxycarbamimidoyl}—1,2,5—oxadiazol—3—yl)oxy]cyclobutyl}acetamide, N—{cis—3—[(4—{N—[(7S)—4—fluorobicyclo[4.2.0]octa—1,3,5—trien—7—yl]—N'—hydroxycarbamimidoyl}—1,2,5—oxadiazol—3—yl)oxy]cyclobutyl}—2—hydroxyacetamide, N—{1—[(4—{N—[(7S)—4—fluorobicyclo[4.2.0]octa—1,3,5—trien—7—yl]—N'—hydroxycarbamimidoyl}—1,2,5—oxadiazol—3—yl)oxy]—3—hydroxypropan—2—yl}acetamide, N—{(2S)—2—[(4—{N—[(7S)-4—fluorobicyclo[4.2.0]octa—1,3,5—trien—7—yl]—N'—hydroxycarbamimidoyl}—1,2,5—oxadiazol—3—yl)oxy]propyl}acetamide, methyl {2—[(4—{N—[(7S)—4—fluorobicyclo[4.2.0]octa—1,3,5—trien—7—yl]—N'—hydroxycarbamimidoyl}—1,2,5—oxadiazol—3—yl)oxy]ethyl}carbamate, 4—{[cis—3—(carbamoylamino)cyclobutyl]oxy}—N—[(7S)—4—fluorobicyclo[4.2.0]octa—1,3,5—trien—7—yl]—N'—hydroxy—1,2,5—oxadiazole—3—carboximidamide, N—[(7S)—4—fluorobicyclo[4.2.0]octa—1,3,5—trien—7—yl]—N'—hydroxy—4—{[cis—3—(sulfamoylamino)cyclobutyl]oxy}—1,2,5—oxadiazole—3—carboximidamide, N—[(7S)—4—fluorobicyclo[4.2.0]octa—1,3,5—trien—7—yl]—N'—hydroxy—4—{2—[(3R)—3—hydroxypyrrolidin—1—yl]—2—oxoethoxy}—1,2,5—oxadiazole—3—carboximidamide, N—[(7S)—4—fluorobicyclo[4.2.0]octa—1,3,5—trien—7—yl]—N'—hydroxy—4—{2—[(3S)—3—hydroxypyrrolidin—1—yl]—2—oxoethoxy}1,2,5—oxadiazole—3—carboximidamide, N—{(2S)—2—[(4—{N—[(7S)—4—fluorobicyclo[4.2.0]octa—1,3,5—trien—7—yl]—N'—hydroxycarbamimidoyl}—1,2,5—oxadiazol—3—yl)oxy]propyl}—2—hydroxyacetamide, N—[(7S)—4—fluorobicyclo[4.2.0]octa—1,3,5—trien—7—yl]—N'—hydroxy—4—{[1—(1—hydroxycyclopropane—1—carbonyl)azetidin—3—yl]oxy}—1,2,5—oxadiazole—3—carboximidamide, N—[(7S)—4—fluorobicyclo[4.2.0]octa—1,3,5—trien—7—yl]—N'—hydroxy—4—({1—[(2S)—2—hydroxypropanoyl]azetidin—3—yl}oxy)—1,2,5—oxadiazole—3—carboximidamide, N—[(7S)—4—fluorobicyclo[4.2.0]octa—1,3,5—trien—7—yl]—N'—hydroxy—4—[(1—sulfamoylpiperidin—4—yl)oxy]—1,2,5—oxadiazole—3—carboximidamide, N—[(7S)—4—fluorobicyclo[4.2.0]octa—1,3,5—trien—7—yl]—N'—hydroxy—4—{[1—(hydroxyacetyl)piperidin—4—yl]oxy}—1,2,5—oxadiazole—3—carboximidamide, N—{(2R)—1—[(4—{N—[(7S)—4—fluorobicyclo[4.2.0]octa—1,3,5—trien—7—yl]—N'—hydroxycarbamimidoyl}—1,2,5—oxadiazol—3—yl)oxy]—3—hydroxypropan—2—yl}acetamide, N—{(2S)—1—[(4—{N—[(7S)—4—fluorobicyclo[4.2.0]octa—1,3,5—trien—7—yl]—N'—hydroxycarbamimidoyl}—1,2,5—oxadiazol—3—yl)oxy]—3—hydroxypropan—2—yl}acetamide, N—{(2S)—3—[(4—{N—[(7S)—4—fluorobicyclo[4.2.0]octa—1,3,5—trien—7—yl]—N'—hydroxycarbamimidoyl}—1,2,5—oxadiazol—3—yl)oxy]—2—hydroxypropyl}acetamide, N—[(7S)—4—fluorobicyclo[4.2.0]octa—1,3,5—trien—7—yl]—N'—hydroxy—4—{[(2S)—1—(hydroxyacetyl)azetidin—2—yl]methoxy}—1,2,5—oxadiazole—3—carboximidamide, N—{(2S)—2—[(4—{N—[(7S)—4—fluorobicyclo[4.2.0]octa—1,3,5—trien—7—yl]—N'—hydroxycarbamimidoyl}—1,2,5—oxadiazol—3—yl)oxy]—3—hydroxypropyl acetamide, N—{trans—3—[(4—{N—[(7S)—4—fluorobicyclo[4.2.0]octa—1,3,5—trien—7—yl]—N'—hydroxycarbamimidoyl}—1,2,5—oxadiazol—3—yl)oxy]cyclobutyl}—2—hydroxyacetamide, 4—{[trans—3—(carbamoylamino)cyclobutyl]oxy}—N—[(7S)—4—fluorobicyclo[4.2.0]octa—1,3,5—trien—7—yl]—N'—hydroxy—1,2,5—oxadiazole—3—carboximidamide, N—[(7S)—4—fluorobicyclo[4.2.0]octa—1,3,5—trien—7—yl]—N'—hydroxy—4—{[(2R)—1—(hydroxyacetyl)pyrrolidin—2—yl]methoxy}—1,2,5—oxadiazole—3—carboximidamide, N—[(7S)—4—fluorobicyclo[4.2.0]octa—1,3,5—trien—7—yl]—N'—hydroxy—4—{[1—(hydroxyacetyl)azetidin—3—yl]methoxy}—1,2,5—oxadiazole—3—carboximidamide, and N—[(7S)—4—fluorobicyclo[4.2.0]octa—1,3,5—trien—7—yl]—N'—hydroxy—4—{[(3R)—1—(hydroxyacetyl)pyrrolidin—3—yl]oxy }-1,2,5—oxadiazole—3—carboximidamide.

19. A composition which comprises an inert carrier and a compound of claim 1 or a pharmaceutically acceptable salt thereof.

\* \* \* \* \*